United States Patent
Abell et al.

(10) Patent No.: US 6,630,331 B1
(45) Date of Patent: Oct. 7, 2003

(54) HERBICIDES TEST METHOD

(75) Inventors: Christopher Abell, Cambridge (GB); Alison Gail Smith, Downing Street (GB); Ulrich Genschel, Hamburg (DE); Bernd Laber, Bad Soden (DE)

(73) Assignee: Hoechst Schering AgrEvo GmbH, Berlin (DE)

( * ) Notice: Subject to any disclaimer, the term of this patent is extended or adjusted under 35 U.S.C. 154(b) by 0 days.

(21) Appl. No.: 09/424,378

(22) PCT Filed: Jun. 2, 1998

(86) PCT No.: PCT/EP98/03261

§ 371 (c)(1),
(2), (4) Date: Nov. 23, 1999

(87) PCT Pub. No.: WO99/42565

PCT Pub. Date: Aug. 26, 1999

(30) Foreign Application Priority Data

May 31, 1997 (GB) .............................................. 9711163
Jun. 27, 1997 (GB) .............................................. 9713477

(51) Int. Cl.[7] .......................... C12N 9/00; C12N 1/20; C12N 15/00; C07H 21/04; C07H 21/02
(52) U.S. Cl. .................... 435/183; 435/325; 435/320.1; 435/252.3; 435/6; 435/252.33; 536/23.2; 536/24.31; 536/24.32
(58) Field of Search .............................. 536/23.2, 24.31, 536/24.32; 435/252.3, 320.1, 6, 252.33, 325, 183

(56) References Cited

PUBLICATIONS

Sambrook et al., Molecular Cloning, 2nd edition, Cold Spring Harbor Lab. Press, 1989.*
Genschel et al., Biochem. J. (1999), 341, 669–678.
Genschel et al., Comparison of the Biosynthetic Pathways Leading to Pantothenate (vitamin $B_5$) in Bacteria and Higher Plants, Abstract No. XP–002092389, 1995.
Jones et al. "Cloning and Sequencing of the *Escherichia coli* pan BGene, Which Encodes Ketopantoate Hydromethyltransferase, and Overexpression of the Enzyme", Journal of Bacteriology, vol. 175, No. 7, pp. 2125–2130, Apr. 1993, Abstract No. XP–002092390.
Jones et al. "Evidence for the Pathway to Panthothenate in Plants", Canadian Journal of Chemistry, vol. 72, No. 1, pp. 261–263, 1994, Abstract No. XP–002092391.
Lanzetta et al., "An Improved Assay for Nanomole Amounts of Inorganic Phosphate", Analytical Biochemistry, vol. 100, No. 1, pp. 95–97, 1979, Abstract No. XP–002092392.
Chifflet et al., "A Method for the Determination of Inorganic Phosphate in the Presence fo Labile Organic Phosphate and High Concentrations of Protein: Application to Lens ATPases", Analytical Biochemistry, vol. 168, No. 1, pp. 1–4, 1988, Abstract No. XP–002092393.
Miyatake et al. "Enzymological Properties of Pantothenate Synthetase From *Escherichia Coli B*", Journal of Nutritional Science and Vitaminology, vol. 24, No. 3, pp. 243–253, 1978, Abstract No. XP–002092394.
Cronan et al., "Genetic and Biochemical Analyses of Pantothenate Biosynthesis in *Escherichia coli* and *Salmonella typhimurium*", Journal of Bateriology, vol. 149, No. 3, pp. 916–922, 1982, Abstract No. XP–002092395.
Database EMBL Nucleotide and Protein Sequences, Aug. 1, 1997, Abstract No. XP–002092396.
Database WPI, Derwent Publications ltd., Jan. 10, 1997, Abstract No. XP–002092397.
Database EMBL Nucleotide and Protein Sequences, Aug. 1, 1997, Abstract No. XP–002092569.

* cited by examiner

*Primary Examiner*—M. Monshipouri
(74) *Attorney, Agent, or Firm*—Frommer Lawrence & Haug LLP

(57) ABSTRACT

An isolated DNA molecule encoding a protein from a plant, which protein has pantothenate synthetase activity; a non-naturally occuring chimeric gene comprising a promoter operably linked to a DNA molecule encoding a protein from a plant having pantothenate synthetase activity; a recombinant vector comprising the chimeric gene wherein the vector is capable of being stably transformed into host cell, a host cell stably transformed with a vector wherein the host cell is capable of expressing the DNA molecule; a method for assaying a protein having pantothenate synthetase activity; the use as herbicides of compounds which inhibit pantothenate synthetase, and a herbicidal composition, comprising one or more active ingredients which show significant pantothenate synthetase inhibition in an assay, are disclosed.

The invention relates to plant enzymatic activity, and aspects therefor, involved in the biosynthesis of coenzyme A. The invention particularly relates to the plant enzyme known either as pantoate B-alanine ligase, pantoate activating enzyme or pantothenate synthetase (PS).

9 Claims, 18 Drawing Sheets

FIG. 2A

| FIG. 2A |
|---------|
| FIG. 2B |

FIG. 2

```
EcoRI         start
GAATTCGGCAGCTCCAATGGCACCAATGGTGATATCTGATAAGGACGAGATGCGGAAATGGTCAAGGTCCATGCGATCCAAGGCAAGCTCATCGCC  -
              M  A  P  M  V  I  S  D  K  D  E  M  R  K  W  S  R  S  M  R  S  Q  G  K  L  I  A CTCGTCCCACCACATGGCCTTCCTCAGAAGGCCACCTTCTCTCGTCAGAGAGGCTCACAACCAGCTGACCTCGTCGCCGTCTCAATCTATGTCAACC  -
L  V  P  T  M  G  F  L  H  E  G  H  L  S  L  V  R  D  A  H  N  H  A  D  L  V  A  V  S  I  Y  V  N  P CTGGCCAGTTGTTCCCGACCGAGACTTTCGCATACCCTTCGATTTCAAGGTGATCCAAAAACTCATGTCTGTTCCTGGTGGTGTTGATGTTGT  -
G  Q  F  S  P  T  E  D  L  S  A  Y  P  S  D  F  Q  G  D  L  Q  K  L  M  S  V  P  G  G  V  D  V  V TTTCACCCCCACATTGTATGATTACGGTGGTGATGCGGTGATGCGGTGATGGGGGTGGTGTCTGTGTTGTAGGAGAGACT  -
F  H  P  H  N  L  Y  D  Y  G  G  D  G  G  D  A  V  E  C  G  G  D  G  V  V  S  C  V  D  R  R  S GGTTTGGGGGATGAAACTTGGCGTTAGAGCTGAAGAGCTGAGAAAGTAGGCCCTGTTTCTTAGAGGGTTGCCACCATTGTTA  -
G  F  G  H  E  T  W  V  R  A  E  K  L  E  K  P  L  C  G  K  S  R  P  V  F  F  R  G  V  A  T  I  V  T
                                                                                    BglII
CCAAGTGTGTTAATATTGTGAGCCTGATGTTGCTGTCTGTCTTTGGGAGAAGGACTATCAGCAATGAAAATTATTCAGAGAATGTTCAGATCTGATTT  -
                                                                                    ↑
K  L  F  N  I  V  E  P  D  V  A  V  F  G  K  K  D  Y  Q  Q  W  K  I  I  Q  R  M  V  R  D  L  D  F TTCCATAAAGTGATAGGTTCTGAAGTAATACCTGAGAAAGATGGCCTAGCAATGAGTTCCCGTAATGTGTACCTATCACCTGAAGAGGGAAAGGCA  -
S  I  K  V  I  G  S  E  V  I  R  E  K  D  G  L  A  M  S  S  R  N  V  Y  L  S  P  E  E  R  E  K  A GTATCTATAAATAATCATTGTTAGCTAATCGGCAGCAGAGAATGGCAGAAGATACATTGTGAGAAATTGATAACTTGTCGTGCAAACTATCACCG  -
V  S  I  N  K  S  L  F  R  A  K  S  A  A  E  D  G  Q  I  H  C  E  K  L  I  N  L  V  V  Q  S  I  T  E AAGCTGGTGGAAGGATTGATTATGCTGAGATTGTTGATCAAAATAATTGGAGAAAGTGAATGATCAAGGCTCCTGTGTCTTCGTGTTTCTGCATG  -
A  G  G  R  I  D  Y  A  E  I  V  D  Q  N  N  L  E  K  V  E  W  I  K  G  P  V  V  F  C  V  S  A  W GTTTGGGAAAGCAGGCTTATAGACATAGAAATCAACTTGTAATGAAGTAAGATTGATCTAACCTGTGAATAATCTCAGACAATGACCATATGA  -
F  G  K  A  R  L  I  D  N  I  E  I  N  L  *

TTAGTAGTTCTGCATTTCATGGGGTATAGACTTCATTCTACAAGCCATGATATGACTACTTGTAGATGTATTTACTACCTCATGAAATTCTAGGAGCT  -
```

FIG. 2

| FIG. 2A |
|---|
| FIG. 2B |

FIG. 2B

GCTTCTATTGTTGCTGATGGTATATATATTTGCAGAGAGCCACCACTCCAGAGAGGAAAACAAAATTAGAGAAATCTTGCTTATGTATCAAAGTGCCCCAGGT

TTACTCATTAATCTAGATAAATCTGAGCTTTCTTAGGCTGATCTACGCCTAGAGAGCCCTAGAGATAGACAAACATAATTCTGTGCTGATAAAATTAACGCATTGA

TTCCCATTTGAAATAAAAAAAAAAAAAAAAAAAACTCGAG
XhoI

FIG. 4

| FIG. 4A |
| --- |
| FIG. 4B |

| FIG. 4 | FIG. 4A |
|---|---|
| | FIG. 4B |

FIG. 4B

```
                                                                                        ClaI
AGCAAGAAAGTTGGTCCCTGTAGAACAGATCGACGGCCCTGTGGTCCTGTGGTTCCGGCTTGGAAAGGTCAGGCTGATCGATATATCGAAAT   - 1000
 Q  E  S  L  V  P  V  E  Q  I  D  G  P  V  V  I  C  V  A  A  W  F  G  K  V  R  L  I  D  N  I  E  I

ClaI
CGATACACGATCCTCAGGTTTGGGGGGATTCACTCGCTGCTGTCGTTGAAATACCTTTGTTGTTCGGTGATGATTCGCGTC   - 1100
 D  T  R  S  *

ATGTTGTACGCTGTAACAATCACAGAGAGAAAAATATGCAGGATTACACTGACTGAAGGCAAATTTATATAGTACAAACTGTAGAGGCCTGATGCTGTAACA   - 1200
                                                                NotI
GGGGAAATCATGCTTGTTGATTACAGATTCCGCTGAAAAAAAAAAAAAAAAAAGGGGCGGC   - 1264
```

| FIG. 6A |
|---------|
| FIG. 6B |

```
lotus   ------------------------------------------------------------
rice    --------------------------PVSPCPLLSDSSPLIDWTTMAAPREPEVIRDKAMRAWS----
coli    ------------------------------------------------VLIIETLPLLRQQI----
pombe   ------------------------------------------------MQVLKEKLLIHQQV----
subt    ------------------------------------------------------------
syne    ------------------------------------------------MRQITDISQLKEAI----
yeast   ------------------------------------------------VQVFKTIAGLQTY----
                                                                  ** lotus   ------MNISRCSVHIYVYKKWCVLIHCFIQVFILHIHIELMKIFHIVEEVVQWRTQELRETRPRETIGFVP
rice    ------------------------------------------------------
                                                                  .

lotus   TMGFLHEGHLSLVRDAHNHAD------LVAVSIYVNPGQFSPTEDLSAYPSDFQGDLQKLMSVPGGVDVVFH
rice    TMGYLHQGHLSLISAAAAAASADPVAIVVTIYVNPSQFAPSEDLATYPSDFAGDLRKLAS-TGVVDAVFN
coli    TMGNLHDGHMKLVDEAKARAD------VVVVSIFVNPMQFDRPEDLARYPRTLQEDCEKLNKR--KVDLVFA
pombe   TMGNLHEGHFSLVREAKRHAE------KVVVSIFVNPMQFNPQDLLLYPRTMDQDCSQLQNL--GVDLVYA
subt    TMGFLHEGHLTLADKARQEND------AVIMSIFVNPAQFGPNEDFEAYPRDIERDAALABNA--GVDILFT
syne    TMGSLHAGHGSLLKRAVABHD------LVVLSIFVNPLQFGPGEDLEKYPRDFDGDRQWAESL--GVAVIFA
yeast   TMGCLHSGHASLISQSVKENT------YTVVSIFVNPSQFAPTEDLDNYPRTLPDDIKLLESL--KVDVLFA
        ***  **  **          *         .*.***  **    *         **       *  ..

lotus   P-----HNLYDYG------GDGDAVAECGGDGVVSCVDRRSGFGHETWVRAEKLEKPLCGKSRPVFFRGV
rice    P-----PDLVRG------AGRRGA------GSGGAISCLEEAAGDGHETWVRVERLEKGLCGASRPVFFRGV
coli    P5V---KEIYPNG------TBT-------------------------HTYVDVPGLSTMLEGASRPGHFRGV
pombe   PTV---EELYPEG------SQD-------------------------IIFVDVPKLSTMLEGASRPGHFRGV
subt    PDA---HDMYP-------GEK-------------------------NVTIHVERRTDVLCGRSREGHFDGV
syne    PTVTDLGIDAKG------DQT-------------------------TVLPPPAMTEVLCGAHRPGHPQGV
yeast   PNA---HVMYPQGIPLDIEEQK-----------------------GPPVSVLGLSEKLEGKTRPNFFRGV
        *   *   **                                              *  *  *** lotus   ATIVTKLFNIVEPDVAVFGKKDYQQMKIIQRAVRDLDFSIKVIGSEVIREKDGLAMSSRNVYLSPEEREK
rice    ATIVSKLFNIIEPDVPVFGKKDYQQMRVLLPYWSGLDFGIEIMGSRNCARTDGLAMNSRNVHLSREEGKK
```

| FIG. 6 | FIG. 6A |
|---|---|
|  | FIG. 6B |

FIG. 6B

```
coli    STIVSKLFNLVQPDIACFGEKDFQQLALIRKHVADHGFDIEIVGVPIMRAKDGLALSSRNGYLTAEQRKI
pombe   TTVVSKLFHIVNPDVACFGEKDFQQVAIKKMVRDLMFFIEIIQVFIVRADDGLALSSRNGYLTSEERKI
subt    AIVLTKLFNLVKFTRAYFGLKDAQQVAVDGLISDFFNDIELVPVDTVREEDGLAKSSRNVYLTAEERKS
syne    ATIVTKLFTIVCPDVAYFGAKDAQQLAIIRRLVQDLMLTVTIRSCATVREKSGLAMSSRNQYLSPIEKEQ
yeast   ATVVTKLFNIVMADVAYFGQKDIQQFIVLQCMVDELFVNTRLQMMPIVRMNNGLALSSRNKYLCPESLKI
          :  ***  .     **  **  **   :            .                 *** *** *.

lotus   AVSINKSLFRAKSAA------EDGQIHCEKLINLVVQS--------ITEAGGRIDYAEIVDQNNLEKVEWIKG----
rice    ALSISRSLVDARTGA------LKGNTDSKQIKMKIVQT--------LFETGGQVDYVEIVEQESLVPVEQIDG----
coli    APGLYKVLSSIADKL------QAGERDLDEIITIAGQE--------LNEKGFRADDIQIRDADTLLEVSETSK----
pombe   APNLYKILKLKLAQEL-----SNGNGDLEKLIAETNTE--------LSRCRFIPDQLEICDSTTLEPFTAGTK----
subt    APKLYRALQTSAELV------QAGERDPEAVIKAAKDI--------IETTSGTIDYVELYSYPELEPVNEIAG----
syne    ATVLYRSLQAAPTAI------SSRRSPS----------------FCFVDRHPGREPGRGTVLSRCNICNMMKLTPC-
yeast   SENLYRGLKAAENAIRRLAPGGRLSRSEIIDTVTQIWAPYVDSHDFKIDYVSLADFKTLDELSDVENTSE
          .  :           *                  .                                    .

lotus   PVVFCVSANFGK--------------ARLIDNIEINL--------
rice    PVVICVAANFGK--------------VRLIDNIEIDTRS------
coli    RAVILVAAWLGD--------------ARLIDNRMVELA-------
pombe   NVVILAAAWLGK--------------ARLIDNIQTTIN-------
subt    KMILAVAVAFSK--------------ARLIDNIIDIREMERI
syne    -QPITWNITGPKSCFNGDR-------RLCG---------------
yeast   QQPIVISCAVYVTDREKPDTVVRLIDNIVI---------------
                                  **
``` coli
pombe
subt
syne
yeast lotus
rice
coli
pombe
subt
syne
yeast lotus
rice
coli
pombe
subt
syne
yeast

FIG. 8

| FIG. 8A |
| FIG. 8B |

| FIG. 8 |
|---|
| FIG. 8A |
| FIG. 8B |

TTCACGCTTGATGACTTTTTTTAGCGGCTGAAGGACGACAATCCCATCGCTCAAAACACAAATATGAAGGACAAATCGTCTTTCACACTTTGCA

TAGTAAAGCAAAGTTTATATACTTCAGCAAAGTTGAAGTTGAAGTCTGAAGTTCGTGCTTTCTCAAATATCTTAGATCACCGTCTGTCTAGAGCAT

ATATCTATTGTTGACGCACCCCTTTTACAAAAAAAAAAAAAGAAAACAGAAACGATCTATTAAGTAATAAAAAAGTTATTTAGAAAATAAGGTGCAGTAAGCTT¶

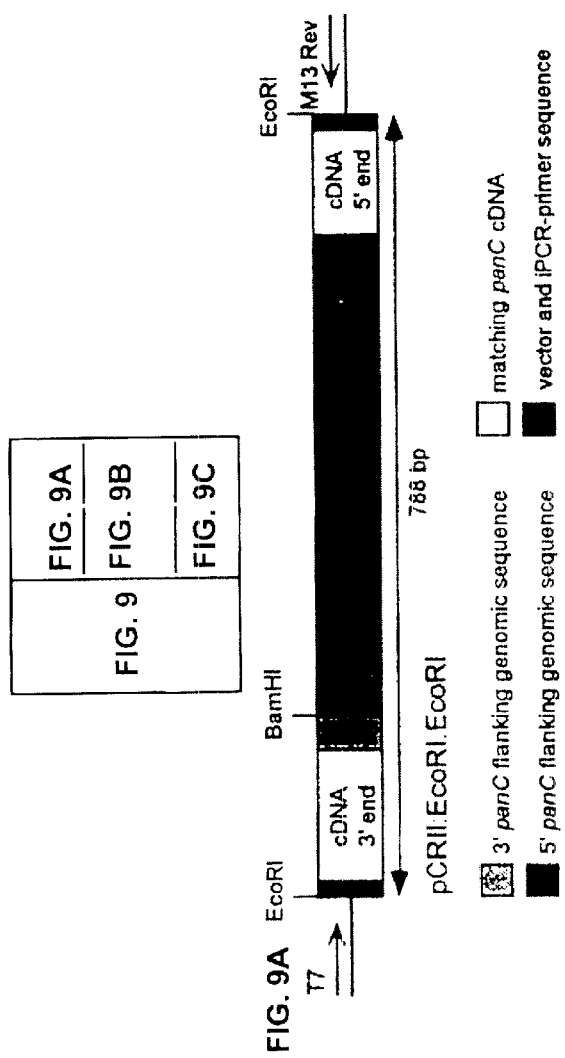

FIG. 9C

| | |
|---|---|
| | FIG. 9A |
| FIG. 9 | FIG. 9B |
| | FIG. 9C |

```
401  ...ACTACCTCTCTCCAGTCGTTCGCTCGAGCTCCAACCTCCCTCACCCCCGTTCCCCTTCCCTCCTACCCCCTTCGTGGGTAG
481  ...TCTTGGTCGAATCTTCCCGGATCAATATCATATATGATATCATCATTTCAATAGAATGAAGGCGCCACCTATCTATTT
561  ...GCTTCATCAAAAGCCCTTCTTTGCAAGAGTTCCATTGTTCTTATCACCTTCAGTTCAACTAGCTTTACACTTTTTCG
                                                               ¶ 5' start of cDNA --> ...
                                                                      start panC ORF
                                                                    M H A P M V I S D K D E M R K W S
641  ACATTCCCAATAACAACACCAGAACCCTCCCCAATGCACCCAATGGTGATATCTGATAAGGACGAGATGCGGAAATGT
     stop
           ... matching panC cDNA (bases 1 - 101)
                                                                              EcoRI
721  CAAGGTCCATGCGATCCCAAGGCAAGCTCATGCCCGTTGCCACCATGGATCCGAAGCCGAATTC 3'
                  L15 primer (reverse complement)
      R   S   M   R   S   Q   G   K   L   I   A   L   V   P   T   M
```

FIG. 10

| FIG. 10A |
|----------|
| FIG. 10B |

FIG. 10A

5'---RBS---TSE---ATGGCACCAATGGTGATATCTGAT-3'
                 |||||||||||||||||||||||
GAATTCGGCGAGCTCCAATGGCACCAGCTCGATAAGGACGAGAAATGTCAAGTCCATGCGAT
                            M  A  P  H  V  I  S  D  K  D  E  K  R  K  W  S  R  S  M  R  S

CCCAAGGCAAGCTCATCGCCCTGGTTCCGACCATGGGCTTCCTTCACGAAGCCACCTTTCTCTCGTCAGAGACGGCTCAC
 Q  G  K  L  I  A  L  V  P  T  M  G  F  L  H  E  G  H  L  S  L  V  R  D  A  H

AACCACGCTGACCTGGTCGCGGTCTCAATCTATGTCAAACTATGTCAAAACTCATGTCGTCTGTTCCTGGTGATGTGTTTCCACCCCACAATTGT
 N  H  A  D  L  V  A  V  S  I  Y  V  N  P  G  Q  F  S  P  T  E  D  L  S  A  Y  P

TTCTGATTTCAAGGTGATCTCCAAAACTCATGTCGTCTGTTCCTGGTGATGTGTTTCCACCCCACAATTGTATAGGAGAGT
 S  D  F  Q  G  D  L  Q  K  L  M  S  V  P  G  G  V  D  V  V  F  H  P  H  N  L  Y

ATGATTACGGTGGTGATGGCGGTGATGCGTGGCGGAGTCGTGGCCGGAGTCTGGAGGGGTGGTCGTGGCGGAGTGAGAGCCTGTTTTCTTAG
 D  Y  G  G  D  G  C  D  A  V  A  E  C  G  G  D  G  V  V  S  C  V  D  R  R  S

GGTTTGGGCATGAAACTTGGGTTAGAGCTGGAAGCTGGAGAACCCTTGTGGGAAGAGTAGGCCCTGTTTTCTTAG
 G  F  G  H  E  T  W  V  R  A  E  K  L  E  K  P  L  C  G  K  S  R  P  V  F  F  R

AGGGGTTGCCACCATTGTTACCAAGTTGTTTAATATTGTGGAGCCTGATGTGCTGTGTTGGAAGAAGGACTATCAGC
 G  V  A  T  I  V  T  K  L  F  N  I  V  E  P  D  V  A  V  F  G  K  K  D  Y  Q  Q

AATGAAAATTATTCAGAGAATGGTTCGAGATCTTGATTTTCCATAAAGTGATAGGTTCTGAAGTAATACGTGAGAAA
 W  K  I  I  Q  R  M  V  R  D  L  D  F  S  I  K  V  I  G  S  E  V  I  R  E  K

GATGGCCTAGCAATGAGTTCCGGTAATGTGTACCTATCACCTGAAGAGAGGAAAAGGCAGTATCTATAAATCATT

FIG. 10

| FIG. 10A |
|----------|
| FIG. 10B |

FIG. 10B

D G L A M S S R N V Y L S P E E R E K A V S I N K S L
GTTTAGAGCTAAATCGGCAGCAGAAGATGACAGATACATTGTGAGAAATTGATAAACTTGGTGTGCAAGTATCACCG

F R A K S A A E D G Q I H C E K L I N L V V Q S I T E
AAGCTGGTGGAAGGATTGATTATGCTGAGATTGTTGATCAAATATTTGGAGAAAGTGGAATGGATCAAGGGTCCTGTT

A G G R I D Y A E I V D Q N N L E K V E W I K G P V
GTCTTCTGTGTTTCTGCATGGTTTGGGAAAGCCAAGGCTTATAGACAACATAGAAATCAACTTGTAAATGGAAGTAAGATT

3'-TTGTATCTTTAGTTGAACATT---5' *

V F C V S A W F G K A R L I D N I E I N L *
GATCTAACCTGTGAATAATCTCAGACATGACCATATGATTAGTAGTTCTGCATTTCATGGGTATAGACTTCATTCT

ACAAGCCATGATATGACTACTGTAGATGTATTTTACTACCTCATGAAATTCTAGAGCTGCTTCTATTGTTGGTGATG

GTATAATATTTGCAGAGCCACCACTCCAGAGGAAACAAATTAGAGAAATCTGCTTATGTATCAAAGTGCCCCAGGT

TTACTCATTAATCTAGATAAATCTGAGCTTTCTTAGGCTGATGTACGCCTAGAGATAGACAAACATAATTCTGGTGCTG

GATAAAATTAACGCATTGATTCCCATTTGAAATAAAAAAAAAAAAAAAAACTCGAG

Anion exchange chromatography of recombinant *Lotus japonicus* pantothenate synthetase

FIG. 12
High-throughput assay for recombinant *Lotus japonicus* pantothenate synthetase.
Protein dependence and time course of the pantothenate synthase assay.
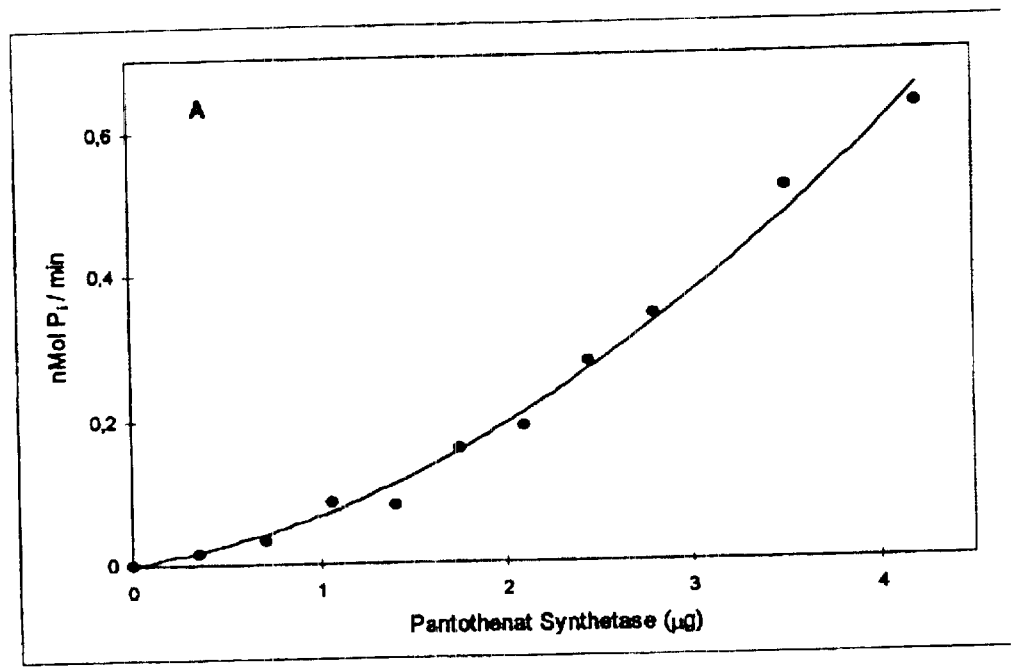
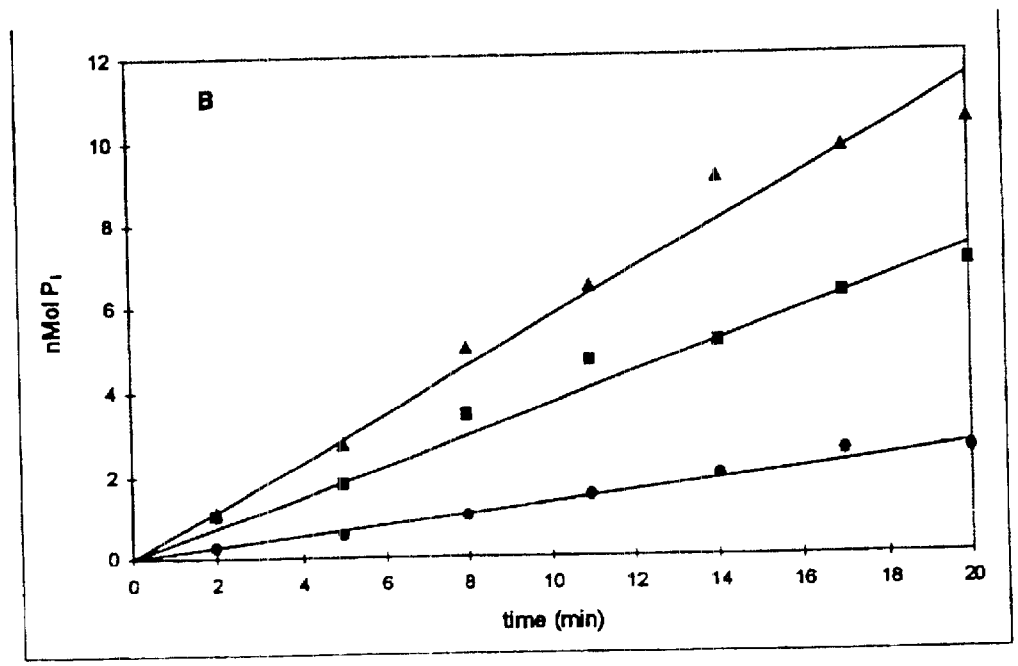

SEQUENCE LISTING

<160> NUMBER OF SEQ ID NOS: 21

<210> SEQ ID NO 1
<211> LENGTH: 1338
<212> TYPE: DNA
<213> ORGANISM: Lotus japonicus

<400> SEQUENCE: 1

```
gaattcggca cgagctccaa tggcaccaat ggtgatatct gataaggacg agatgcggaa      60
atggtcaagg tccatgcgat cccaaggcaa gctcatcgcc ctcgttccca ccatgggctt     120
ccttcacgaa ggccacctttt ctctcgtcag agacgctcac aaccacgctg acctcgtcgc    180
cgtctcaatc tatgtcaacc ctggccagtt ttccccgacc gaggaccttt ccgcataccc     240
ttctgatttt caaggtgatc tccaaaaact catgtctgtt cctggtggtg ttgatgttgt     300
tttccacccc cacaatttgt atgattacgg tggtgatggc ggtgatgctg tggcggagtg     360
tggtggtgat ggggtggtgt cttgtgttga taggaggagt ggttttgggc atgaaacttg     420
ggttagagct gagaagctgg agaaacccct ttgtgggaag agtaggcctg ttttctttag     480
aggggttgcc accattgtta ccaagttgtt taatattgtg gagcctgatg ttgctgtgtt     540
tgggaagaag gactatcagc aatggaaaat tattcagaga atggttcgag atcttgattt     600
ttccataaaa gtgataggtt ctgaagtaat acgtgagaaa gatggcctag caatgagttc     660
ccgtaatgtg tacctatcac ctgaagagag ggaaaaggca gtatctataa ataaatcatt     720
gtttagagct aaatcggcag cagaagatgg acagatacat tgtgagaaat tgataaactt     780
ggtcgtgcaa agtatcaccg aagctggtgg aaggattgat tatgctgaga ttgttgatca     840
aaataatttg gagaaagtgg aatggatcaa gggtcctgtt gtcttctgtg tttctgcatg     900
gtttgggaaa gccaggctta tagacaacat agaaatcaac ttgtaaatgg aagtaagatt     960
gatctaacct tgtgaataat ctcagacatg gaccatatga ttagtagttc tggcatttca    1020
tggggtatag acttcattct acaagccatg atatgactac ttgtagatgt attttactac    1080
ctcatgaaat tctaggagct gcttctattt gttggtgatg gtataatatt ttgcagagcc    1140
accactccag aggaaaacaa aattagagaa atcttgctta tgtatcaaag tgccccaggt    1200
ttactcatta atctagataa atctgagctt tctttaggct gatgtacgcc tagagataga    1260
caaacataat tctggtgctg gataaaatta acgcattgga ttcccatttg aaataaaaaa    1320
aaaaaaaaaa aactcgag                                                  1338
```

<210> SEQ ID NO 2
<211> LENGTH: 1264
<212> TYPE: DNA
<213> ORGANISM: Oryza sativa -continued

```
<400> SEQUENCE: 2
gtcgacccac gcgtccggtt tctccctgtc cacttctgtc cgattcctcc tcacctctta      60
tcgattggac gaccatggcg gcgccgcgcg agccggaggt gatccgcgac aaggcggcga     120
tgcgcgcatg gtcgcgccgc cgtcgcgccg agggcaagac cgtcgcggtc gtacccacca     180
tgggctacct ccaccaaggc cacctctccc tcatctccgc cgccgccgcc gccgcctccg     240
ctgatcccgt cgccatcgtc gtcaccatct acgtcaaccc cagccagttc gcgccctcag     300
aggacctcgc cacctaccct tccgacttcg ccggtgacct ccgcaagctc gcctccaccg     360
gcgtcgtgga tgccgtcttc aaccccctg acctctacgt ccgtggcgcc ggtcgccgcg      420
gggccggctc cggaggcgcg atctcctgcc tggaggaggc ggccggggat gggcacgaga     480
cgtgggttcg ggtggagcga ttggagaagg gattgtgcgg ggccagccgt cccgtgttct     540
tccgaggcgt ggccaccata gtctccaagc tgtttaacat catcgagccg gatgttcctg     600
tgttcgggaa gaaggattat cagcagtggc gcgtcatctt gccgtattgg tcgggacttg     660
attttggcat agagataatg ggatcaagaa attgtgcgag aactgatggt cttgccatga     720
actcccggaa tgtgcaccta tcacgcgagg aagggaaaaa ggcattatcc atcagtagat     780
cactggttga tgctagaact ggcgccttga agggaaacac tgattccaaa caaatcaaaa     840
acaaaatagt acagacacta actgaaactg gcggtcaggt tgactatgtt gagatcgtgg     900
agcaagaaag tttggtccct gtagaacaga tcgacggccc tgtggtcatt tgcgttgcgg     960
cgtggtttgg aaaggtcagg ctgatcgata atatcgaaat cgatacacga tcctgaggtt    1020
ttggggggat tcacttgctg tctgctgtga ccttggcatt gcgtttgaaa taccttttgt    1080
ttcgcgtgat gattcgcgtc atgttgtacg ctgtaacaat cacagagaga aaatatgcag    1140
gagtacactg actgaaggca aatttataag tacaaactgt agaggcctga tgctgtaaca    1200
ggggaaatca tgcttgttga ttacagattc cgctgaaaaa aaaaaaaaaa aaagggcgg    1260
ccgc                                                                 1264

<210> SEQ ID NO 3
<211> LENGTH: 1500
<212> TYPE: DNA
<213> ORGANISM: Saccharomyces cerevisiae

<400> SEQUENCE: 3
gatatccggg taaatgttac tttaacgagt ttttttcttt tgtcatattt tccaacaaga      60
gattaatgaa catttctcga tgtagcgtac atatttatgt gtacaagaag tggtgtgtgt     120
tgatactgca ctgttttata caagttttta tactgcatat ccatatagaa ttgatgaaaa     180
tcttccatac tgtcgaagaa gttgttcaat ggagaacaca ggagctgagg gaaactagat     240
ttagagaaac tattgggttc gttcccacaa tgggttgcct gcattcgggt cacgctagtt     300
tgatctcgca gtctgtgaag gaaaacacct atactgtggt cagtatattt gtaaatccct     360
cccagtttgc gccaacggaa gatctagata actatcctcg aactttgcca gacgacatca     420
aattgcttga gtcgttgaag gtggatgttc tatttgctcc taatgcacac gtgatgtatc     480
cacagggaat tccgctcgac atagaagagc agaaaggccc ttttgttagt gttcttggat     540
tgagtgaaaa attagagggg aagacgagac ctaacttctt taggggcgtg caactgtcg      600
tgactaaact attcaatatc gttatggcg atgtggctta ttttgggcag aaggacattc      660
aacagttcat tgttttacag tgtatggtgg acgaactgtt gttaataca aggctacaaa      720
tgatgcctat tgtaagaaac aataatggac tggctctgag tagtagaaac aaatatcttt      780
```

```
gtccagagtc tttaaagatc tctgaaaacc tttaccgcgg gctgaaagct gcggaaaatg    840
ctattaggag actagcacca gggggacgtc tctccagatc agaaatcatc gatactgtga    900
ctcaaatatg ggcaccctac gttgattccc acgatttcaa aatcgactat gtttccttag    960
cagattttaa gactcttgat gaactctccg atgttgaaaa caccagcgaa cagcagccaa   1020
tagtcattag ttgtgctgta tacgtgactg accgcgaaaa acccgatacg gtcgtcagac   1080
taatagataa catcgttatt taaactaggt gattgggcct tcccgtgtct gtgttgcagt   1140 ataccact cttatacagt atgcacgata ttcttttaaa ccaacaacgg gatgatagat     1200
ttcacgcttg atgactttt ttttagacgg ctgaagggac gacatcccca tcgctcaaaa    1260
cacaaatatg gaaaggacaa atcgtctttc acagtttgca tagtaaaagc aaagtttata   1320
ctacttcagc aaagttgaag ttgtttggca cttgtttcgt gctttctcaa atatcttaga   1380
tcaccgtctg tctagagcat atatctattg tttgacgcac ccctttaca aaaaaaaaa    1440 aaagaaacag atctattaag taataaaaaa gttatttagg aaataaggtg cagtaagctt   1500
```

<210> SEQ ID NO 4
<211> LENGTH: 308
<212> TYPE: PRT
<213> ORGANISM: Lotus japonicus

<400> SEQUENCE: 4

```
Met Ala Pro Met Val Ile Ser Asp Lys Asp Glu Met Arg Lys Trp Ser
1               5                   10                  15

Arg Ser Met Arg Ser Gln Gly Lys Leu Ile Ala Leu Val Pro Thr Met
                20                  25                  30

Gly Phe Leu His Glu Gly His Leu Ser Leu Val Arg Asp Ala His Asn
            35                  40                  45

His Ala Asp Leu Val Ala Val Ser Ile Tyr Val Asn Pro Gly Gln Phe
        50                  55                  60

Ser Pro Thr Glu Asp Leu Ser Ala Tyr Pro Ser Asp Phe Gln Gly Asp
65                  70                  75                  80

Leu Gln Lys Leu Met Ser Val Pro Gly Gly Val Asp Val Val Phe His
                85                  90                  95

Pro His Asn Leu Tyr Asp Tyr Gly Gly Asp Gly Asp Ala Val Ala
                100                 105                 110

Glu Cys Gly Gly Asp Gly Val Val Ser Cys Val Asp Arg Arg Ser Gly
            115                 120                 125

Phe Gly His Glu Thr Trp Val Arg Ala Glu Lys Leu Glu Lys Pro Leu
        130                 135                 140

Cys Gly Lys Ser Arg Pro Val Phe Phe Arg Gly Val Ala Thr Ile Val
145                 150                 155                 160

Thr Lys Leu Phe Asn Ile Val Glu Pro Asp Val Ala Val Phe Gly Lys
                165                 170                 175

Lys Asp Tyr Gln Gln Trp Lys Ile Ile Gln Arg Met Val Arg Asp Leu
            180                 185                 190

Asp Phe Ser Ile Lys Val Ile Gly Ser Glu Val Ile Arg Glu Lys Asp
        195                 200                 205

Gly Leu Ala Met Ser Ser Arg Asn Val Tyr Leu Ser Pro Glu Glu Arg
    210                 215                 220

Glu Lys Ala Val Ser Ile Asn Lys Ser Leu Phe Arg Ala Lys Ser Ala
225                 230                 235                 240

Ala Glu Asp Gly Gln Ile His Cys Glu Lys Leu Ile Asn Leu Val Val
```

```
                        245                 250                 255
Gln Ser Ile Thr Glu Ala Gly Gly Arg Ile Asp Tyr Ala Glu Ile Val
            260                 265                 270

Asp Gln Asn Asn Leu Glu Lys Val Glu Trp Ile Lys Gly Pro Val Val
            275                 280                 285

Phe Cys Val Ser Ala Trp Phe Gly Lys Ala Arg Leu Ile Asp Asn Ile
            290                 295                 300

Glu Ile Asn Leu
305

<210> SEQ ID NO 5
<211> LENGTH: 313
<212> TYPE: PRT
<213> ORGANISM: Oryza sativa

<400> SEQUENCE: 5

Met Ala Ala Pro Arg Glu Pro Glu Val Ile Arg Asp Lys Ala Ala Met
1               5                   10                  15

Arg Ala Trp Ser Arg Arg Arg Ala Glu Gly Lys Thr Val Ala Val
            20                  25                  30

Val Pro Thr Met Gly Tyr Leu His Gln Gly His Leu Ser Leu Ile Ser
            35                  40                  45

Ala Ala Ala Ala Ala Ser Ala Asp Pro Val Ala Ile Val Val Thr
50                  55                  60

Ile Tyr Val Asn Pro Ser Gln Phe Ala Pro Ser Glu Asp Leu Ala Thr
65                  70                  75                  80

Tyr Pro Ser Asp Phe Ala Gly Asp Leu Arg Lys Leu Ala Ser Thr Gly
            85                  90                  95

Val Val Asp Ala Val Phe Asn Pro Pro Asp Leu Tyr Val Arg Gly Ala
            100                 105                 110

Gly Arg Gly Ala Gly Ser Gly Ala Ile Ser Cys Leu Glu Glu
            115                 120                 125

Ala Ala Gly Asp Gly His Glu Thr Trp Val Arg Val Glu Arg Leu Glu
            130                 135                 140

Lys Gly Leu Cys Gly Ala Ser Arg Pro Val Phe Phe Arg Gly Val Ala
145                 150                 155                 160

Thr Ile Val Ser Lys Leu Phe Asn Ile Ile Glu Pro Asp Val Pro Val
            165                 170                 175

Phe Gly Lys Lys Asp Tyr Gln Gln Trp Arg Val Ile Leu Pro Tyr Trp
            180                 185                 190

Ser Gly Leu Asp Phe Gly Ile Glu Ile Met Gly Ser Arg Asn Cys Ala
            195                 200                 205

Arg Thr Asp Gly Leu Ala Met Asn Ser Arg Asn Val His Leu Ser Arg
            210                 215                 220

Glu Glu Gly Lys Lys Ala Leu Ser Ile Ser Arg Ser Leu Val Asp Ala
225                 230                 235                 240

Arg Thr Gly Ala Leu Lys Gly Asn Thr Asp Ser Lys Gln Ile Lys Asn
            245                 250                 255

Lys Ile Val Gln Thr Leu Thr Glu Thr Gly Gly Gln Val Asp Tyr Val
            260                 265                 270

Glu Ile Val Glu Gln Glu Ser Leu Val Pro Val Glu Gln Ile Asp Gly
            275                 280                 285

Pro Val Val Ile Cys Val Ala Ala Trp Phe Gly Lys Val Arg Leu Ile
            290                 295                 300
```

```
Asp Asn Ile Glu Ile Asp Thr Arg Ser
305                 310
```

```
<210> SEQ ID NO 6
<211> LENGTH: 283
<212> TYPE: PRT
<213> ORGANISM: Escherichia coli

<400> SEQUENCE: 6

Val Leu Ile Ile Glu Thr Leu Pro Leu Leu Arg Gln Gln Ile Arg Arg
1               5                   10                  15

Leu Arg Met Glu Gly Lys Arg Val Ala Leu Val Pro Thr Met Gly Asn
            20                  25                  30

Leu His Asp Gly His Met Lys Leu Val Asp Glu Ala Lys Ala Arg Ala
        35                  40                  45

Asp Val Val Val Ser Ile Phe Val Asn Pro Met Gln Phe Asp Arg
    50                  55                  60

Pro Glu Asp Leu Ala Arg Tyr Pro Arg Thr Leu Gln Glu Asp Cys Glu
65                  70                  75                  80

Lys Leu Asn Lys Arg Lys Val Asp Leu Val Phe Ala Pro Ser Val Lys
                85                  90                  95

Glu Ile Tyr Pro Asn Gly Thr Glu Thr His Thr Tyr Val Asp Val Pro
            100                 105                 110

Gly Leu Ser Thr Met Leu Glu Gly Ala Ser Arg Pro Gly His Phe Arg
        115                 120                 125

Gly Val Ser Thr Ile Val Ser Lys Leu Phe Asn Leu Val Gln Pro Asp
    130                 135                 140

Ile Ala Cys Phe Gly Glu Lys Asp Phe Gln Gln Leu Ala Leu Ile Arg
145                 150                 155                 160

Lys Met Val Ala Asp Met Gly Phe Asp Ile Glu Ile Val Gly Val Pro
                165                 170                 175

Ile Met Arg Ala Lys Asp Gly Leu Ala Leu Ser Ser Arg Asn Gly Tyr
            180                 185                 190

Leu Thr Ala Glu Gln Arg Lys Ile Ala Pro Gly Leu Tyr Lys Val Leu
        195                 200                 205

Ser Ser Ile Ala Asp Lys Leu Gln Ala Gly Glu Arg Asp Leu Asp Glu
    210                 215                 220

Ile Ile Thr Ile Ala Gly Gln Glu Leu Asn Glu Lys Gly Phe Arg Ala
225                 230                 235                 240

Asp Asp Ile Gln Ile Arg Asp Ala Asp Thr Leu Leu Glu Val Ser Glu
                245                 250                 255

Thr Ser Lys Arg Ala Val Ile Leu Val Ala Ala Trp Leu Gly Asp Ala
            260                 265                 270

Arg Leu Ile Asp Asn Lys Met Val Glu Leu Ala
        275                 280
```

```
<210> SEQ ID NO 7
<211> LENGTH: 286
<212> TYPE: PRT
<213> ORGANISM: Bacillus subtilis

<400> SEQUENCE: 7

Met Arg Gln Ile Thr Asp Ile Ser Gln Leu Lys Glu Ala Ile Lys Gln
1               5                   10                  15

Tyr His Ser Glu Gly Lys Ser Ile Gly Phe Val Pro Thr Met Gly Phe
            20                  25                  30
```

-continued

Leu His Glu Gly His Leu Thr Leu Ala Asp Lys Ala Arg Gln Glu Asn
            35                  40                  45

Asp Ala Val Ile Met Ser Ile Phe Val Asn Pro Ala Gln Phe Gly Pro
        50                  55                  60

Asn Glu Asp Phe Glu Ala Tyr Pro Arg Asp Ile Glu Arg Asp Ala Ala
65                  70                  75                  80

Leu Ala Glu Asn Ala Gly Val Asp Ile Leu Phe Thr Pro Asp Ala His
                85                  90                  95

Asp Met Tyr Pro Gly Glu Lys Asn Val Thr Ile His Val Glu Arg Arg
            100                 105                 110

Thr Asp Val Leu Cys Gly Arg Ser Arg Glu Gly His Phe Asp Gly Val
        115                 120                 125

Ala Ile Val Leu Thr Lys Leu Phe Asn Leu Val Lys Pro Thr Arg Ala
    130                 135                 140

Tyr Phe Gly Leu Lys Asp Ala Gln Gln Val Ala Val Val Asp Gly Leu
145                 150                 155                 160

Ile Ser Asp Phe Phe Met Asp Ile Glu Leu Val Pro Val Asp Thr Val
                165                 170                 175

Arg Glu Glu Asp Gly Leu Ala Lys Ser Ser Arg Asn Val Tyr Leu Thr
            180                 185                 190

Ala Glu Glu Arg Lys Glu Ala Pro Lys Leu Tyr Arg Ala Leu Gln Thr
        195                 200                 205

Ser Ala Glu Leu Val Gln Ala Gly Glu Arg Asp Pro Glu Ala Val Ile
    210                 215                 220

Lys Ala Ala Lys Asp Ile Ile Glu Thr Thr Ser Gly Thr Ile Asp Tyr
225                 230                 235                 240

Val Glu Leu Tyr Ser Tyr Pro Glu Leu Glu Pro Val Asn Glu Ile Ala
                245                 250                 255

Gly Lys Met Ile Leu Ala Val Ala Val Ala Phe Ser Lys Ala Arg Leu
            260                 265                 270

Ile Asp Asn Ile Ile Ile Asp Ile Arg Glu Met Glu Arg Ile
        275                 280                 285

<210> SEQ ID NO 8
<211> LENGTH: 275
<212> TYPE: PRT
<213> ORGANISM: Synechocystis sp

<400> SEQUENCE: 8

Val Gln Val Phe Arg Thr Ile Ala Gly Leu Gln Thr Tyr Leu Arg Gln
1               5                   10                  15

Ala Gly Arg Gly Lys Thr Val Gly Leu Val Pro Thr Met Gly Ser Leu
            20                  25                  30

His Ala Gly His Gly Ser Leu Leu Lys Arg Ala Val Ala Glu Met Asp
        35                  40                  45

Leu Val Val Leu Ser Ile Phe Val Asn Pro Leu Gln Phe Gly Pro Gly
    50                  55                  60

Glu Asp Leu Glu Lys Tyr Pro Arg Asp Phe Asp Gly Asp Arg Gln Trp
65                  70                  75                  80

Ala Glu Ser Leu Gly Val Ala Val Ile Phe Ala Pro Thr Val Thr Asp
                85                  90                  95

Leu Gly Ile Asp Ala Lys Gly Asp Gln Thr Thr Val Leu Pro Pro Pro
            100                 105                 110

Ala Met Thr Glu Val Leu Cys Gly Ala His Arg Pro Gly His Phe Gln
        115                 120                 125

```
Gly Val Ala Thr Ile Val Thr Lys Leu Phe Thr Ile Val Cys Pro Asp
    130                 135                 140

Val Ala Tyr Phe Gly Ala Lys Asp Ala Gln Gln Leu Ala Ile Ile Arg
145                 150                 155                 160

Arg Leu Val Gln Asp Leu Asn Leu Thr Val Thr Ile Arg Ser Cys Ala
                165                 170                 175

Thr Val Arg Glu Glu Ser Gly Leu Ala Met Ser Ser Arg Asn Gln Tyr
            180                 185                 190

Leu Ser Pro Ile Glu Lys Glu Gln Ala Thr Val Leu Tyr Arg Ser Leu
        195                 200                 205

Gln Ala Ala Pro Thr Ala Ile Ser Ser Arg Arg Ser Pro Ser Phe Cys
210                 215                 220

Phe Val Asp Arg His Pro Gly Arg Phe Gly Arg Gly Thr Val Leu Ser
225                 230                 235                 240

Arg Cys Asn Ile Cys Asn Trp Trp Lys Leu Thr Pro Cys Gln Pro Ile
                245                 250                 255

Thr Trp Asn Ile Thr Gly Pro Lys Ser Cys Phe Asn Gly Asp Arg Arg
            260                 265                 270

Leu Cys Gly
        275

<210> SEQ ID NO 9
<211> LENGTH: 345
<212> TYPE: PRT
<213> ORGANISM: Saccharomyces cerevisiae

<400> SEQUENCE: 9

Met Asn Ile Ser Arg Cys Ser Val His Ile Tyr Val Tyr Lys Lys Trp
1               5                   10                  15

Cys Val Leu Ile Leu His Cys Phe Ile Gln Val Phe Ile Leu His Ile
                20                  25                  30

His Ile Glu Leu Met Lys Ile Phe His Thr Val Glu Glu Val Val Gln
            35                  40                  45

Trp Arg Thr Gln Glu Leu Arg Glu Thr Arg Phe Arg Glu Thr Ile Gly
50                  55                  60

Phe Val Pro Thr Met Gly Cys Leu His Ser Gly His Ala Ser Leu Ile
65                  70                  75                  80

Ser Gln Ser Val Lys Glu Asn Thr Tyr Thr Val Val Ser Ile Phe Val
                85                  90                  95

Asn Pro Ser Gln Phe Ala Pro Thr Glu Asp Leu Asp Asn Tyr Pro Arg
            100                 105                 110

Thr Leu Pro Asp Asp Ile Lys Leu Leu Glu Ser Leu Lys Val Asp Val
        115                 120                 125

Leu Phe Ala Pro Asn Ala His Val Met Tyr Pro Gln Gly Ile Pro Leu
130                 135                 140

Asp Ile Glu Glu Gln Lys Gly Pro Phe Val Ser Val Leu Gly Leu Ser
145                 150                 155                 160

Glu Lys Leu Glu Gly Lys Thr Arg Pro Asn Phe Phe Arg Gly Val Ala
                165                 170                 175

Thr Val Val Thr Lys Leu Phe Asn Ile Val Met Ala Asp Val Ala Tyr
            180                 185                 190

Phe Gly Gln Lys Asp Ile Gln Gln Phe Ile Val Leu Gln Cys Met Val
        195                 200                 205

Asp Glu Leu Phe Val Asn Thr Arg Leu Gln Met Met Pro Ile Val Arg
```

```
            210                 215                 220
Asn Asn Asn Gly Leu Ala Leu Ser Ser Arg Asn Lys Tyr Leu Cys Pro
225                 230                 235                 240

Glu Ser Leu Lys Ile Ser Glu Asn Leu Tyr Arg Gly Leu Lys Ala Ala
                245                 250                 255

Glu Asn Ala Ile Arg Arg Leu Ala Pro Gly Gly Arg Leu Ser Arg Ser
                260                 265                 270

Glu Ile Ile Asp Thr Val Thr Gln Ile Trp Ala Pro Tyr Val Asp Ser
                275                 280                 285

His Asp Phe Lys Ile Asp Tyr Val Ser Leu Ala Asp Phe Lys Thr Leu
                290                 295                 300

Asp Glu Leu Ser Asp Val Glu Asn Thr Ser Glu Gln Gln Pro Ile Val
305                 310                 315                 320

Ile Ser Cys Ala Val Tyr Val Thr Asp Arg Glu Lys Pro Asp Thr Val
                325                 330                 335

Val Arg Leu Ile Asp Asn Ile Val Ile
                340                 345

<210> SEQ ID NO 10
<211> LENGTH: 283
<212> TYPE: PRT
<213> ORGANISM: Schizosaccharomyces pombe

<400> SEQUENCE: 10

Met Gln Val Leu Lys Glu Lys Leu Leu Ile His Gln Gln Val Asp Asn
1               5                   10                  15

Trp Arg Lys Asp Gly Asn Arg Ile Ala Phe Val Pro Thr Met Gly Asn
                20                  25                  30

Leu His Glu Gly His Phe Ser Leu Val Arg Glu Ala Lys Arg His Ala
                35                  40                  45

Glu Lys Val Val Val Ser Ile Phe Val Asn Pro Met Gln Phe Asn Asn
                50                  55                  60

Pro Gln Asp Leu Leu Leu Tyr Pro Arg Thr Met Asp Gln Asp Cys Ser
65                  70                  75                  80

Gln Leu Gln Asn Leu Gly Val Asp Leu Val Tyr Ala Pro Thr Val Glu
                85                  90                  95

Glu Leu Tyr Pro Glu Gly Ser Gln Asp Ile Thr Phe Val Asp Val Pro
                100                 105                 110

Lys Leu Ser Thr Met Leu Glu Gly Ala Ser Arg Pro Gly His Phe Arg
                115                 120                 125

Gly Val Thr Thr Val Val Ser Lys Leu Phe His Ile Val Asn Pro Asp
130                 135                 140

Val Ala Cys Phe Gly Glu Lys Asp Phe Gln Gln Val Ala Ile Ile Lys
145                 150                 155                 160

Lys Met Val Arg Asp Leu Asn Phe Phe Ile Glu Ile Gln Val Pro
                165                 170                 175

Ile Val Arg Ala Asp Asp Gly Leu Ala Leu Ser Ser Arg Asn Gly Tyr
                180                 185                 190

Leu Thr Ser Glu Glu Arg Lys Ile Ala Pro Asn Leu Tyr Lys Ile Leu
                195                 200                 205

Lys Lys Leu Ala Gln Glu Leu Ser Asn Gly Asn Gly Asp Leu Glu Lys
                210                 215                 220

Leu Ile Ala Glu Thr Asn Thr Glu Leu Ser Arg Cys Arg Phe Ile Pro
225                 230                 235                 240
```

Asp Gln Leu Glu Ile Cys Asp Ser Thr Leu Glu Pro Phe Thr Ala
            245                 250                 255

Gly Thr Lys Asn Val Val Ile Leu Ala Ala Ala Trp Leu Gly Lys Ala
            260                 265                 270

Arg Leu Ile Asp Asn Ile Gln Thr Thr Ile Asn
            275                 280

<210> SEQ ID NO 11
<211> LENGTH: 788
<212> TYPE: DNA
<213> ORGANISM: Lotus japonicus

<400> SEQUENCE: 11

| | | |
|---|---|---|
| gaattcggct tcatcaagct tatgtatcaa agtgccccag gtttactcat taatctagat | 60 |
| aaatctgagc tttctttagg ctgatgtacg cctagagata gacaaacata attctggtgc | 120 |
| tggataaaat taacgcattg gattcccatt tgaaatatct tggtctccct attttatagg | 180 |
| aggatccaac ggcagagaac ctaggttctc atgacccctc ttgagggcca tcctagcttc | 240 |
| gggatctcat ataaaaggtc ccttacaaca agggccaat gtaacttctc ttagctcaat | 300 |
| tactttgata acttagactt ttcatcctgc tgaaccagaa ttgacttagg catcaaagtg | 360 |
| gtttgcacga ccccctcccg ggcttacctg tacgttgcag actacctctc tccagtcgtt | 420 |
| cgctcgagct ccaacctccc tcaccccgt tccccttccc tcctacccct cgtgggtag | 480 |
| tcttggtcga tcttcccgg atcaatatca tatatgatat catcatcatt tcaatagaat | 540 |
| gaagcgccac ctatctattt gcttcatcaa agccttctt ttgcaagagt tcccatttgt | 600 |
| tcttatcacc ttcacgttca actagcttta cacttttttcg acattcccaa taacaacacc | 660 |
| agaaccctcc tccaatggca ccaatggtga tatctgataa ggacgagatg cggaaatggt | 720 |
| caaggtccat gcgatcccaa ggcaagctca tcgccctcgt tcccaccatg gatcccgaag | 780 |
| ccgaattc | 788 |

<210> SEQ ID NO 12
<211> LENGTH: 33
<212> TYPE: PRT
<213> ORGANISM: Lotus Japonicus

<400> SEQUENCE: 12

Met Ala Pro Met Val Val Ile Ser Asp Lys Asp Glu Met Arg Lys Trp
1               5                   10                  15

Ser Arg Ser Met Arg Ser Gln Gly Lys Leu Ile Ala Leu Val Pro Thr
            20                  25                  30

Met

<210> SEQ ID NO 13
<211> LENGTH: 24
<212> TYPE: DNA
<213> ORGANISM: Lotus japonicus

<400> SEQUENCE: 13
atggcaccaa tggtgatatc tgat                                           24

<210> SEQ ID NO 14
<211> LENGTH: 21
<212> TYPE: DNA
<213> ORGANISM: Lotus japonicus

<400> SEQUENCE: 14

```
ttgtatcttt agttgaacat t                                              21
```

<210> SEQ ID NO 15
<211> LENGTH: 31
<212> TYPE: DNA
<213> ORGANISM: Lotus japonicus

<400> SEQUENCE: 15

```
cgggatccat ggtgggaacg agggcgatga g                                   31
```

<210> SEQ ID NO 16
<211> LENGTH: 30
<212> TYPE: DNA
<213> ORGANISM: Lotus japonicus

<400> SEQUENCE: 16

```
catcaagctt atgtatcaaa gtgccccagg                                     30
```

<210> SEQ ID NO 17
<211> LENGTH: 49
<212> TYPE: DNA
<213> ORGANISM: Lotus japonicus

<400> SEQUENCE: 17

```
cgcgctctag aaggaggaat ttaaaatggc accaatggtg atatctgat                49
```

<210> SEQ ID NO 18
<211> LENGTH: 32
<212> TYPE: DNA
<213> ORGANISM: Lotus japonicus

<400> SEQUENCE: 18

```
gcgcgctcga gttacaagtt gatttctatg tt                                  32
```

<210> SEQ ID NO 19
<211> LENGTH: 17
<212> TYPE: PRT
<213> ORGANISM: Lotus japonicus

<400> SEQUENCE: 19

Met Ala Pro Met Val Ile Ser Asp Lys Asp Glu Met Arg Lys Trp Ser
1               5                   10                  15

Arg

<210> SEQ ID NO 20
<211> LENGTH: 15
<212> TYPE: PRT
<213> ORGANISM: Lotus japonicus

<400> SEQUENCE: 20

Pro Met Val Ile Ser Asp Lys Asp Glu Met Arg Lys Trp Ser Arg
1               5                   10                  15

<210> SEQ ID NO 21
<211> LENGTH: 16
<212> TYPE: PRT
<213> ORGANISM: Lotus japonicus

<400> SEQUENCE: 21

Ala Pro Met Val Ile Ser Asp Lys Asp Glu Met Arg Lys Trp Ser Arg
1               5                   10                  15

HERBICIDES TEST METHOD

CROSS-REFERENCE TO RELATED APPLICATIONS

This application claims priority PCT/EP98/03261, filed Jun. 2, 1998 which in turn claims priority to British patent applications 97 111 63.7 and 97 134 77.9 filed May 31, 1997 and Jun. 27, 1997, respectively.

STATEMENT REGARDING FEDERALLY SPONSORED RESEARCH OR DEVELOPMENT

Not applicable.

FIELD OF THE INVENTION

The invention relates to plant enzymatic activity, and aspects thereof, involved in the biosynthesis of Coenzyme A. The invention particularly relates to the plant enzyme known either as pantoate-β-alanine ligase (EC 6.3.2.1), pantoate activating enzyme or pantothenate synthetase (PS). PS catalyses the synthesis of pantothenate.

BACKGROUND OF THE INVENTION

PS is an essential enzyme in the in planta biosynthesis of the vitamin and Coenzyme A precursor pantothenate. It is known to catalyse the following reaction:

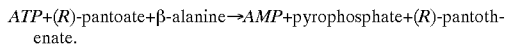

PS genes have previously been isolated from *Escherichia coil* (GenBank accession number P31663), *Bacillus subtilis* (GenBank accession number P52998), and the cyanobacterium Synechocystis (GenBank accession number U44896). DNA sequences from *Saccharomyces cerevisiae* (GenBank accession number P40459) and *Schizosaccharomyces pombe* (GenBank accession number Q09673) having unknown functions have been proposed to code for PS enzymes based on DNA and deduced amino acid sequence similarities. To date, however, no gene has been reported which codes for the PS enzyme in any plant species. It is therefore an object of the invention to identify, isolate and sequence a gene coding for the PS enzyme present in plants.

A number of assays have been reported for measuring PS activity. One assay developed by Maas (1950a and 1950b) uses a microbiological assay of pantothenate based on the ability to promote growth of an *E. coli* pantothenate auxotroph (M99-1, panC). The assay developed by Pfleiderer et al (1960) measures the AMP liberated in the PS reaction. In this assay, myokinase catalyses the production of 2 moles of ADP for each mole of AMP released in pantothenate synthesis using ATP supplied in the assay mixture. Pyruvate kinase then generates 2 moles of pyruvate and ATP for 2 moles of phosphoenolpyruvate and ADP. Finally, lactate dehydrogenase reduces 2 moles of pyruvate to yield 2 moles of lactate concomitant with stoichiometric oxidation of NADH to NAD, which can be monitored spectrophotometrically by following the absorbance at 340 nm. A third assay, developed by Miyatake et al (1979), employs an assay mix containing $^{14}$C-β-alanine and unlabelled pantoate. In this assay any $^{14}$C-pantothenate formed is separated from unreacted $^{14}$C-β-alanine by cation exchange chromatography and subsequently quantified by liquid scintillation counting. These assays, however, are not suitable for use with high throughput biochemical screening and cannot be used for the large scale biochemical screening of compounds necessary to discover useful inhibitors of PS.

BRIEF SUMMARY OF THE INVENTION

We have developed an invention which addresses the above-mentioned drawbacks associated with the prior art. Our invention covers a number of related aspects which encompass the same inventive concept.

According to a first aspect of the invention there is provided an isolated DNA molecule encoding a protein from a plant, which protein has PS activity. In preferred embodiments, the DNA is isolated from *Lotus japonicus* or *Oryza sativa*.

To support our invention we herein disclose the cDNA sequence from *Lotus japonicus*. In addition, we have shown that a previously unassigned expressed sequence tag of *Oryza sativa* (GenBank accession number D25017) is part of a cDNA coding sequence for a PS enzyme in *Oryza sativa* and disclose, as part of this invention, the full cDNA sequence of the PS gene from *Oryza sativa*. Furthermore, we have confirmed by sequence similarity, functional complementation of an *Escherichia coli* mutant devoid of PS enzyme activity, and by enzyme assays that the DNA sequence from *Saccharomyces cerevisiae* (GenBank accession number P40459) putatively ascribed as coding for a PS enzyme does code for the PS enzyme of *S. cerevisiae*. A cDNA sequence coding for a PS enzyme in *L. japonicus* is provided in FIG. 2 (SEQ. ID NO:1). A cDNA sequence coding for a PS enzyme in *O. sativa* is provided in FIG. 4 (SEQ ID NO:2). A DNA sequence coding for a PS enzyme in *S. cerevisiae* is provided in FIG. 8 (SEQ ID NO:3). As a result of our invention it is now possible to obtain the DNA coding sequence for the PS enzyme(s) from any plant source using methods available to those skilled in the art.

A further preferred embodiment of this aspect of our invention is an isolated DNA molecule encoding a protein from *L. japonicus* having PS activity wherein said protein comprises the amino acid sequence set forth in FIG. 2 (SEQ ID NO:4). A still further embodiment is an isolated DNA molecule encoding a protein from *O. sativa* having PS activity wherein said protein comprises the amino acid sequence in FIG. 4 (SEQ ID NO:5).

In addition, we have extended our invention to include a further aspect so as to provide a non-naturally occurring chimeric gene comprising a promoter operably linked to a DNA molecule encoding a protein from a plant having PS activity. Preferably, the protein is isolated from a dicotyledonous or a monocotyledonous plant, such as *L. japonicus* or *O. sativa*. Preferably the amino acid sequence is selected from the group set forth in FIG. 2 (*L. japonicus*) and FIG. 4 (*O. sativa*).

We have developed our invention into another aspect which provides a recombinant vector comprising a chimeric gene, wherein the vector is capable of being stably transformed into a host cell. Also comprised in this aspect is the host cell stably transformed with the vector wherein the host cell is preferably a cell selected from the group consisting of a bacterial cell, a yeast cell, and an insect cell and is further capable of expressing the DNA molecule according to the invention.

In a still further aspect we have applied our invention to the recombinant production of the PS enzyme. In particular, the invention provides a method of producing a protein having PS activity in a host organism by firstly inserting a DNA sequence encoding a protein having PS activity into an expression cassette designed for the chosen host; inserting the resultant molecule, containing the individual elements linked in proper reading frame, into a vector capable of being transformed into the host cell; growing the thus transformed host cell in a suitable culture medium; and isolating the protein product either from the transformed cell or the culture medium, or both, and purifying it.

In addition, we have developed our invention to provide methods for assaying a protein having pantothenate synthetase activity comprising; incubating pantothenate synthetase in a suitable reaction mixture in which pantothenate synthetase is capable of catalysing the conversion of pantoate, □-alanine and ATP to pantothenate, AMP and pyrophosphate; determining the amount of pyrophosphate formed by a calorimetric technique based on the assay for pyrophosphate developed by Chang et al. (1983); or converting the pyrophosphate formed by the catalytic activity of the pantothenate synthetase into inorganic phosphate by the catalytic activity of an inorganic pyrophosphatase, preferably yeast inorganic pyrophosphatase; and determining the amount of inorganic phosphate generated by the catalytic activity of said inorganic pyrophosphatase by calorimetric techniques, preferably by techniques based either on the assay for inorganic phosphate developed by Lanzetta et al. (1979) or on the assay for inorganic phosphate developed by Chifflet et al. (1988).

The production of PS, for example by using the recombinant methodology described hereinabove, has enabled us to develop methods of using purified PS to screen for novel inhibitors of PS activity which may be used as herbicides to control undesirable vegetation in fields where crops are grown, particularly agronomically important crops such as maize and other cereal crops such as wheat, oats, rye, sorghum, rice, barley, millet, turf and forage grasses, and the like, as well as cotton sugar cane, sugar beet, oilseed rape, and soybeans.

BRIEF DESCRIPTION OF THE DRAWINGS

FIG. 1A: The L. japonicus pantotheate synthetase cDNA (pLC) was isolated by functional complementation of E. coli AT1371 (panC). FIG. 1B represents the sub-clones needed for the DNA sequencing strategy which is summarized in FIG. 1C.

Referring to FIG. 2, there is shown the nucleotide sequence of the L. japonicus cDNA for pantothenate synthetase and its predicted amino acid sequence. FIGS. 2A and 2B show the DNA sequence of the 1.33 kb EcoRI to XhoI insert of pLC (SEQ ID NO: 1) (described in FIG. 1). The open reading frame codes for a polypeptide of 308 amino acids with a predicted molecular mass of 34.2 kDa (SEQ ID NO: 4) and with 61% similarity to PS from E. coli. The indicated translation start site is putative and the stop codon (TAA) is translated as "*". This ORF on pLC is in frame with lacZ which accounts for expression of functional enzyme in E. coli and hence the observed complementation effect Referring to FIG. 3, there is shown a partial restriction map (FIG. 3A), subcloning (FIG. 3B), and nucleotide sequencing (FIG. 3C) of the rice pantothenate synthetase cDNA. The original cDNA for rice gene, pRC1, was subcloned in order to obtain its complete nucleotide sequence. The arrows indicate the position, direction, and length of individual sequencing runs. The open arrow indicates the EST sequence (GenBank accession no. D25017).

Referring to FIGS. 4A and 4B, there is shown the nucleotide sequence of the rice cDNA for pantothenate synthetase and its predicted amino acid sequence. The figure shows the DNA sequence of the 1.26 kb SalI to NotI insert of pRC1 (FIG. 3) (SEQ ID NO: 2). The ORF encodes a polypeptide of 313 residues with a predicted molecular mass of 33.9 kD (SEQ ID NO: 5). The indicated translation start site is putative, and the stop codon is translated as "*".

Referring to FIGS. 6A and 6B, the alignment of pantothenate synthetase protein sequences is shown. The PS protein sequences predicted from known (L. japonicus (SEQ ID NO: 4), O. sativa (SEQ ID NO: 5), E. coli (SEQ ID NO: 6), B. subtilis (SEQ ID NO: 7), Synechocystis sp. (SEQ ID NO: 8)) or putative (S. cerevisiae (SEQ ID NO: 9), Schizos. pombe(SEQ ID NO: 10)) genes were aligned using CLUSTAL W(1.5) within the GCG software package. Fully conserved residues are marked "*", functionally conserved ones are marked ".". lotus: L. japonicus, rice: O. sativa, coli: E. coli (GenBank P31663), subt: B. subtilis (GenBank P52998), syne: Synechocystis sp. (GenBank U44896), yeast: S. cerevisiae (GenBank P40459), pombe: Schizos. pombe (GenBank Q09673).

FIG. 7A shows the γ bacteriophage clone 1PM4950 that was obtained from the Sanger Centre, Hinxton Hall, Cambridge, UK, where the yeast PS sequence had been generated. FIGS. 7B and 7C show yeast panC, subcloned in two steps to yield plasmid clone pYC1, where the gene is placed under transcriptional control of the lac promoter. The ORF position is indicated by arrows. A T3-primed sequencing reaction using pYC1 as template confirmed the identity of the EcoRV-HindIII insert of the plasmid.

Referring to FIG. 8, there is shown the nucleotide sequence of the S. cerevisiae genomic DNA fragment for pantothenate synthetase and its predicted amino acid sequence. FIGS. 8A and 8B show the nucleotide sequence of the 1.5 kb EcoRV to HindIII genomic DNA fragment of S. cerevisiae (SEQ ID NO: 3) that forms the insert of pYC1. The predicted amino acid sequence of yeast PS appears below the open reading frame (SEQ ID NO: 9). A Shine-Dalgarno-like sequence upstream of the translation initiation codon that may fortuitously serve as a RBS in E. coli is underlined. §-EcoRV; ¶ HindIII.

Referring to FIG 9, there is shown the inverse PCR product of L. japonicus genomic regions flanking panC. FIG. 9A shows a schematic representation of the iPCR product cloned into pCRII. The EcoRI.EcoRI insert was sequenced using T7 and M13 reverse primers. Both sequence runs were performed in duplicate and spanned ca. 600 bases each. FIGS. 9B and 9C show the nucleotide sequence of the cloned iPCR product (SEQ ID NO: 11) and panC ORF (SEQ ID NO: 12). The indicated matches with panC cDNA mean identical sequences. Positions corresponding to the first base (5'-¶) or the last base (3'- §) of the panC cDNA are marked. Within the 5' flanking genomic sequence, there is a stop-codon in frame with the panC ORF.

Referring to FIGS. 10A and 10B, the expression cassette PCR of L. japonicus pantothenate synthetase, including the 2 primers (SEQ ID NOs: 13 and 14), is shown.

FIG. 11A shows the PS activity profile. Fractions 29 through 32 were pooled to give sample PS-I, and fractions 57 through 60 were pooled to give sample PS-II. FIG. 11B shows the protein elution profile followed by continuous measurement of $A_{280}$ and potassium chloride gradient employed.

Referring to FIG. 12, the results of a high-throughput assay for recombinant *L. japonicus* pantothenate synthetase is depicted graphically. FIG. 12A shows the effect of enzyme concentration on the reaction rate. Specific amounts of MonoQ purified PS-I were assayed as described in Example 9, method 2a. The activity-response is proportional in a range from 1 to 4 μg PS per assay. FIG. 12B shows the time course of inorganic phosphate formation. 1.2 mg (●), 2.4 mg (■), and 3.0 mg (▲) of MonoQ purified PS-I were assayed as described in Example 9, method 2a. The activity-response is proportional in a range from 0 to 20 minutes of incubation.

DETAILED DESCRIPTION OF THE INVENTION

Figure 1:
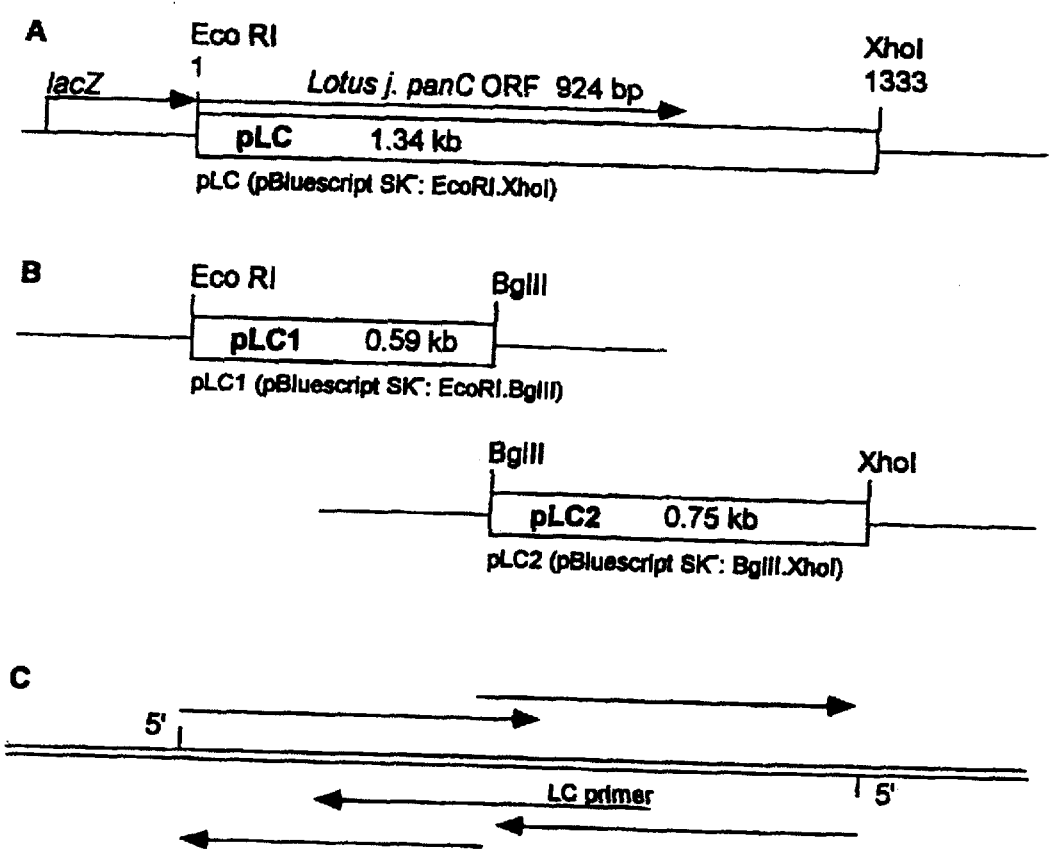
Referring to FIG. 1, there is shown a partial restriction map (FIG. 1A), subcloning (FIG. 1B), and nucleotide sequencing (FIG. 1C) of pLC, a L. japonicus cDNA for pantotheate synthetase.

In particular, the present invention relates to a method for assaying a chemical entity for the ability to inhibit the activity of a PS enzyme from a plant by:
a) combining said PS enzyme in a suitable reaction mixture in which
   i) said PS enzyme is capable of catalysing the conversion of pantoate, β-alanine and ATP to pantothenate, AMP and pyrophosphate;
   ii) the pyrophosphate liberated in the PS reaction is determined by a colorimetric method, preferably by a method based on the assay for pyrophosphate developed by Chang et al. (1983);
   iii) or the pyrophosphate liberated in the PS reaction is further converted to inorganic phosphate by the catalytic activity of an inorganic pyrophosphatase, preferably yeast inorganic pyrophosphatase; and
   iv) the inorganic phosphate generated by the catalytic activity of inorganic pyrophosphatase is determined by a calorimetric method, preferably by a method based on the assay for inorganic phosphate developed by Lanzetta et al. (1979) or by a method based on the assay for inorganic phosphate developed by Chifflet et al. (1983);
b) combining said chemical and said PS enzyme together in a second reaction mixture under the same conditions as in said first reaction mixture; and
c) measuring the amount of pyrophosphate or inorganic phosphate produced in said first and said—second reaction mixture;
wherein said chemical is capable of inhibiting the activity of said PS enzyme if the amount of pyrophosphate or inorganic phosphate measured in said second reaction mixture is significantly less than the amount of pyrophosphate or inorganic phosphate measured in said first reaction mixture.

The assay principle invented here is not limited to measuring PS activity but can be employed to measure any enzyme whose catalytic activity involves the formation of a substrate-nucleotidyl reaction intermediate by transfer of the nucleotidyl moiety from the corresponding nucleoside triphosphate to a suitable substrate, thereby generating inorganic pyrophosphate as one reaction product. Such enzymes include, but are not limited to, all aminoacyl-tRNA synthetases, asparagine synthetase, acetate thiokinase, dephosphocoenzyme-A-pyrophosphorylase and all enzymes catalysing the formation of nucleotide-diphosphate-sugars. The assays are preferably carried out on a microtiter scale and are preferably employed for the high-throughput biochemical screening of inhibitors of the enzymes.

The present invention is further directed to probes capable of specifically hybridising to a plant PS gene, cDNA or mRNA, wherein the probe comprises a contiguous portion of the coding sequence for a PS enzyme from a plant at least 10 nucleotides in length.

A further aspect the invention provides a method of producing a DNA molecule comprising a DNA portion encoding a protein having PS activity by,
a) preparing a nucleotide probe capable of specifically hybridising to a plant PS gene, cDNA or mRNA, wherein the probe comprises a contiguous portion of the coding sequence for a PS enzyme from a plant at least 10 nucleotides in length;
b) probing for other PS coding sequences in populations of cloned genomic DNA fragments or cDNA fragments from a chosen organism using the nucleotide probe prepared according to step a); and
c) isolating a DNA molecule comprising a DNA portion encoding a protein having PS activity.

DNA encoding the PS enzyme may be isolated from any desired plant species according to the invention. One method taught for isolating a plant PS coding sequence is represented by Example 1. In this method cDNA clones encoding a PS enzyme are identified from a library of cDNA clones derived from the plant of interest based on their ability to supply PS enzymatic activity to a mutant host organism deficient in this activity. Suitable host organisms for use in this method are those which can be used to screen cDNA expression libraries and for which mutants deficient in PS activity are either available or can be routinely generated. Such host organisms include, but are not limited to, *E. coli* panC (strain AT1371).

Figures 4, 4A, 4B:
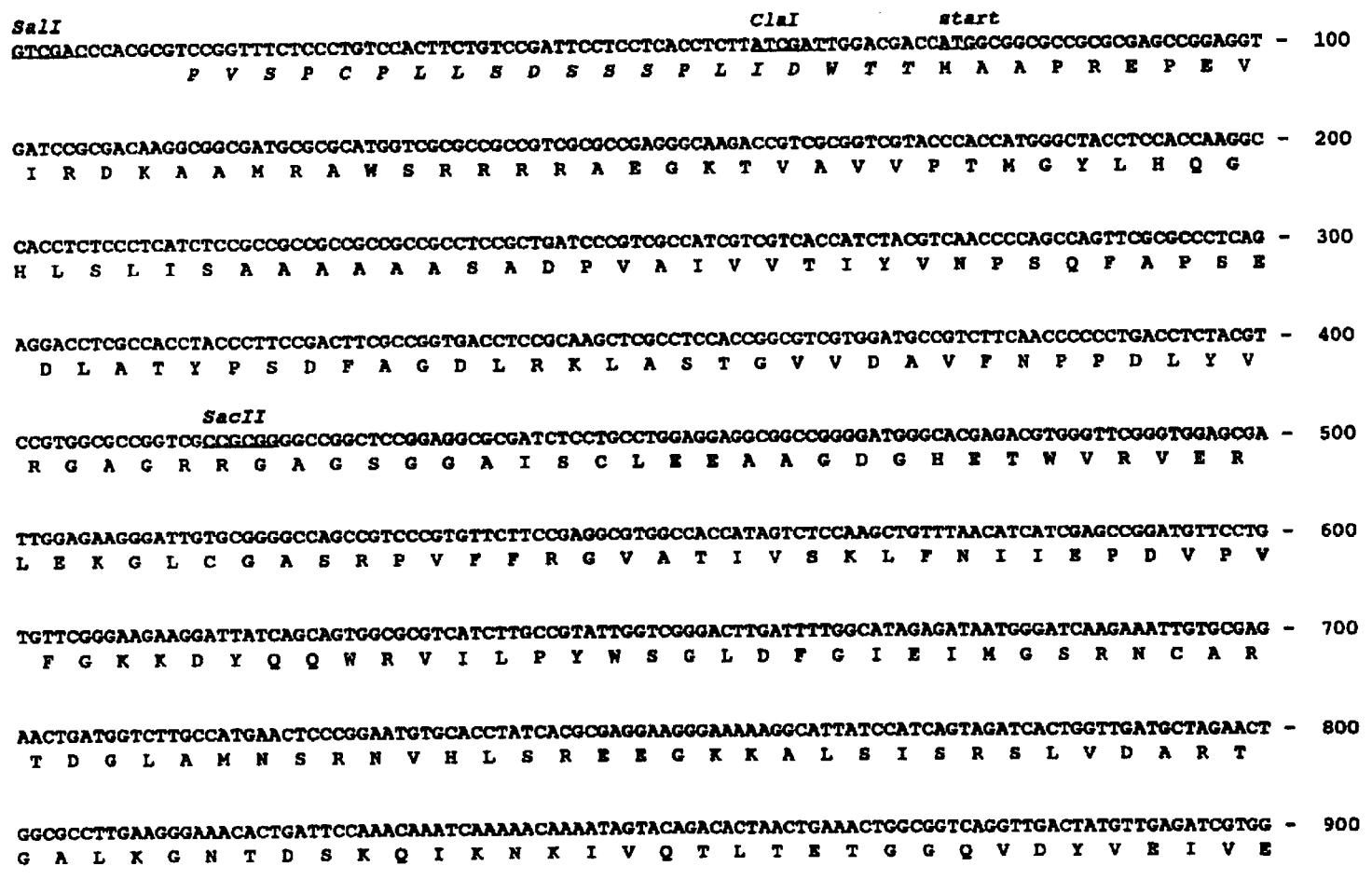

Alternatively, plant PS coding sequences may be isolated according to well known techniques based on their sequence homology to the *Lotus japonicus* PS coding sequence set forth in FIG. 2 or to the *O. sativa* PS coding sequence set forth in FIG. 4. In these techniques all or part of the known PS coding sequence is used as a probe which selectively hybridises to other PS coding sequences present in populations of cloned genomic DNA fragments or cDNA fragments (i.e. genomic or cDNA libraries) from a chosen organism. Such state of the art techniques include hybridisation screening of plated DNA libraries and amplification by PCR using oligonucleotide primers corresponding to sequences conserved among known PS amino acid sequences.

For recombinant production of the PS enzyme in a host organism, the plant PS coding sequence may be inserted into an expression cassette designed for the chosen host and introduced into the host where it is recombinantly produced. The choice of specific regulatory sequences such as promoter, signal sequence, 5' and 3' untranslated sequences, and enhancer appropriate for the chosen host is within the level of skill of those skilled in the art. The resultant molecule, containing the individual elements linked in proper reading frame, may be inserted into a vector capable of being transformed into the host cell. Suitable expression vectors and methods for recombinant production of proteins are well known for host organisms such as *E. coli*, yeast and insect cells. Specific examples include plasmids such as pBLUESCRIPT, pFLAG, pTrcHis, and baculovirus expression vectors, for example those derived-from the genome of *Autographica californica* nuclear polyhedrus virus.

Recombinantly produced plant PS can be isolated and purified using a variety of standard techniques. The actual techniques which may be used will vary depending upon the host organism used, whether the PS enzyme is designed for secretion, and other such factors familiar to those skilled in the art.

Recombinantly produced plant PS is useful for a variety of purposes. For example, it may be used in an in vitro assay to screen known herbicidal chemicals whose target has not been identified to determine if they inhibit PS. Such an in vitro assay may also be used as a more general screen to identify chemicals which inhibit PS activity and which are therefore herbicide candidates. Alternatively, recombinantly produced plant PS may be used to elucidate the complex structure of this enzyme. Such information regarding the structure of the PS enzyme may be used, for example, in the rational design of new inhibitory herbicides.

Typically, the inhibitory effect on PS is determined by a significant reduction, a reduction that is greater than the margin of error inherent in the measurement technique, of pantothenate synthesis in the in vitro assay. Such a determination may be made simply by comparing the amount of pantothenate synthesised in the in vitro assay in the presence and absence of the candidate inhibitor.

The disclosures in British patent applications 97 111 63.7 and 97 134 77.9 from which this application claims priority, and in the abstract accompanying this application are incorporated herein by reference.

The invention will be further described by reference to the following detailed examples. These examples are provided for purposes of illustration only, and are not intended to be limiting unless otherwise specified.

EXAMPLES

A number of standard techniques have been used during development of our invention. These includes: cloning of plant genes by functional complementation (for example Senecoff and Meagher, 1993); the use of inverse PCR to recover fragments of genes not present in conventional libraries (Ocham et al, 1989) and the use of DNA sequence databases to discover PS genes cloned from other species which had unknown function at the time of their submission.

Example 1

Isolation of a cDNA Clone Encoding Pantothenate Synthetase from *L. japonicus*

An *L. japonicus* PS clone was isolated by functional complementation of *E. coli* AT1371 (panC4, Δ(gpt-proA)62, lacY1, tsx-29, glnV44(AS), galK2, λ, rac0, hisG4(Oc), rfbD1, xylA5, mtl-1, argE3(Oc), thi-1, described by Cronan et al, 1982) from a cDNA library (from Corinna Tetzlaff, Department of Plant Sciences, University of Cambridge, Downing Street, Cambridge, CB2 3EA, UK.) The PS cDNA was found in a population of 50,000 ampicillin-resistant transformants of *E. coli* AT1371. The PS clone (pLC), was subcloned and sequenced as summarised in FIG. 1. The resulting nucleotide sequence (FIG. 2) revealed the presence of an open reading frame (ORF) encoding a polypeptide of 308 residues which is 61% similar to the protein sequence of PS from *E. coli*. The open reading frame of PS was in frame with the lacZ on the pBLUESCRIPT vector which probably accounts for the expression of *L. japonicus* PS and hence complementation of *E. coli* AT1371.

Example 2

Isolation of a cDNA Clone Encoding Pantothenate Synthetase from *O. sativa*

Figure 3:
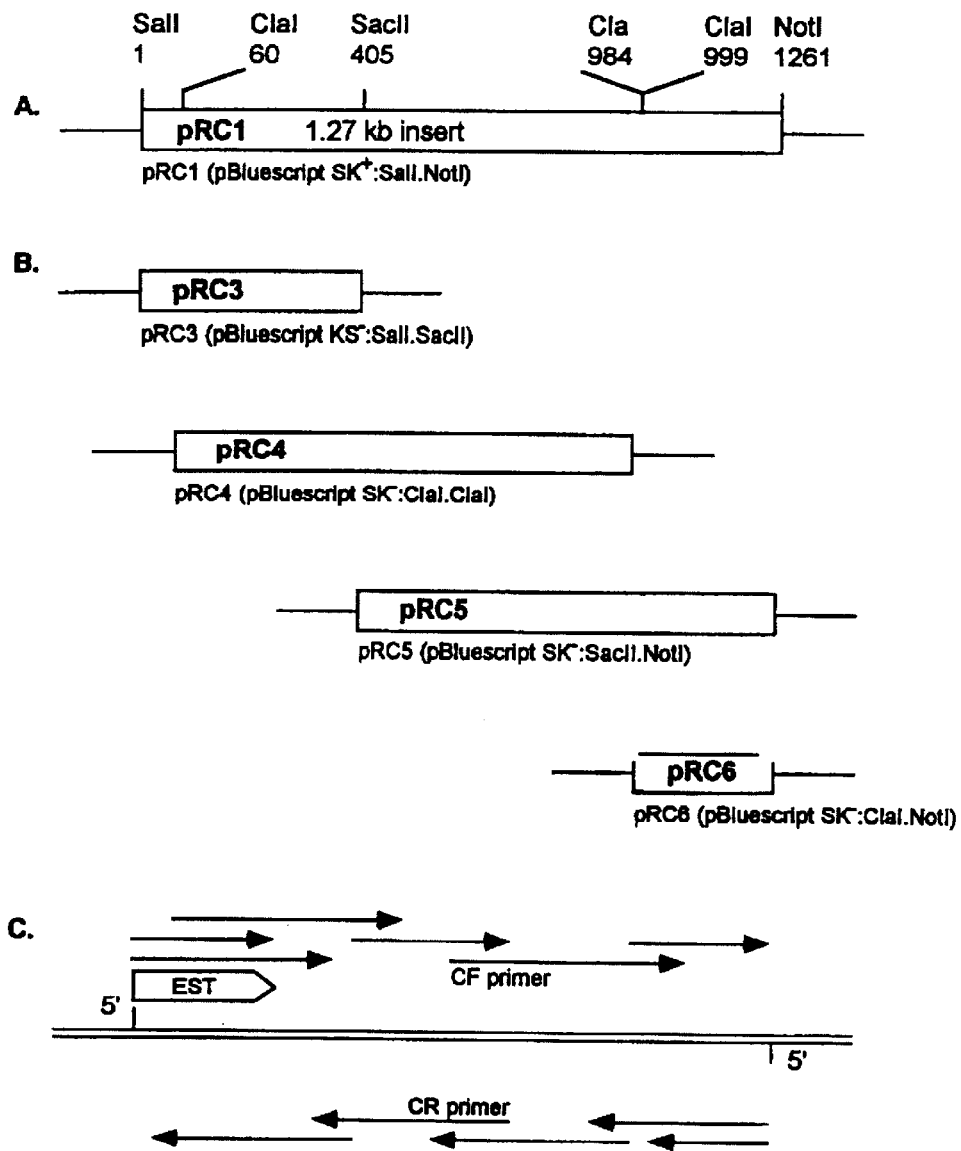
Figure 5:
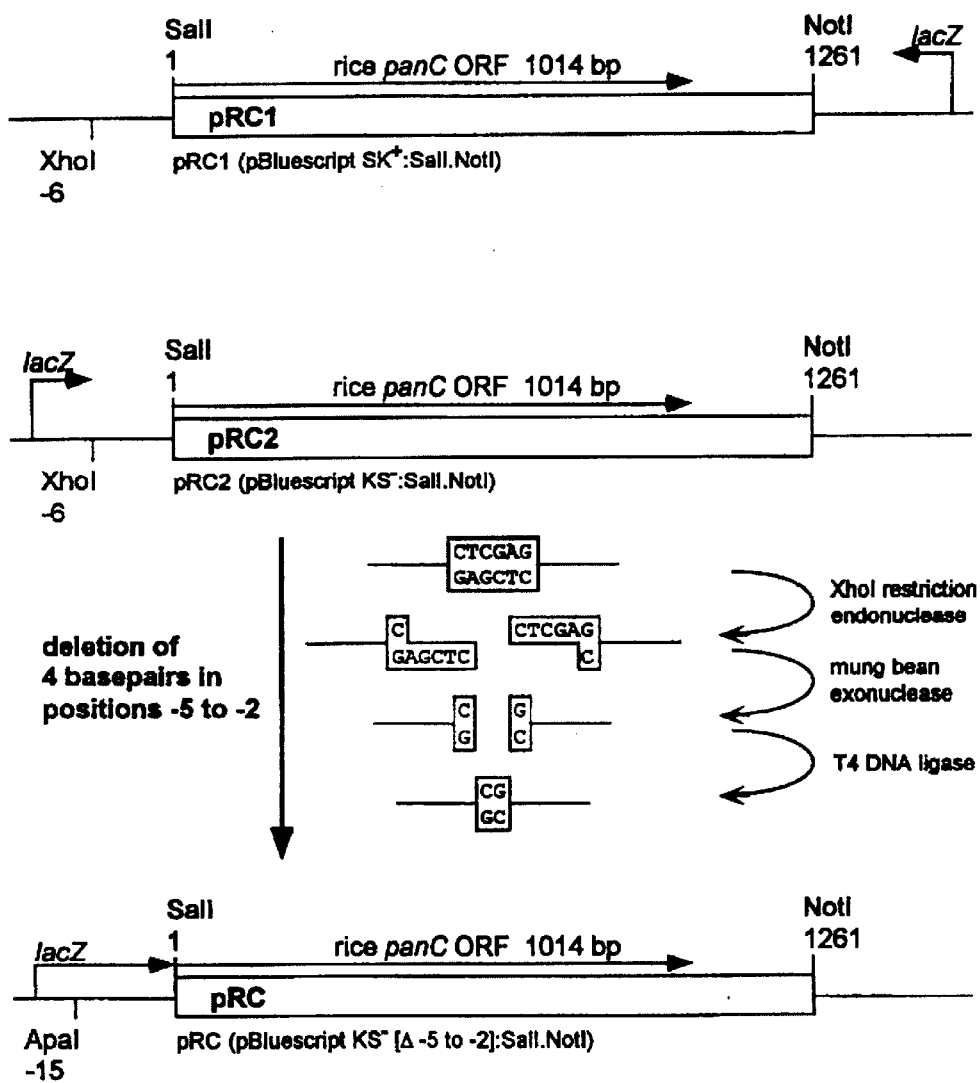
Referring to FIG. 5, there is depicted a method for generating the lacZ-pantothenate synthetase fusion clone for the expression of rice pantothenate synthetase in E. coli. The orientation of the cDNA in pRC1 was changed to yield pRC2 where the open reading frame is under transcriptional control of the lacZ promoter. The lacZ-PS fusion was generated by deleting four base pairs from pRC2, and the resulting plasmid, pRC, was sequenced to confirm the deletion (data not shown).

A PS cDNA sequence from rice was found by nucleotide database searches as an expressed sequence tag (EST) of rice that had been submitted to GenBank (accession number D25017) on behalf of the Japanese Rice Genome Research Program. The full corresponding cDNA clone was obtained from Dr. Yuzo Minobe, National Institute of Agrobiological Resources, Kannondai, Tsukuba Ibaraki, Japan. This cDNA clone was called pRC1 and subcloned and sequenced as shown in FIG. 3. The nucleotide sequence of the 1.3 kb SalI-NotI insert of pRC1 and the predicted amino acid sequence of the PS gene are given in FIG. 4. When this sequence was compared to other PS sequences, the similarity originally seen within the 5' EST region held for the entire open reading frame implying that the rice cDNA in pRC1 does code for PS. However, pRC1 did not complement the *E. coli* panC mutant. Thus, a fusion clone of lacZ and rice PS gene was derived from pRC2 (FIG. 5) that allowed both transcription of the rice cDNA and translation of the protein as a β-galactosidase fusion. Complementation of the *E. coli* panC mutant with the rice pantothenate synthase gene was achieved using this fusion clone.

Example 3

Figure 7:
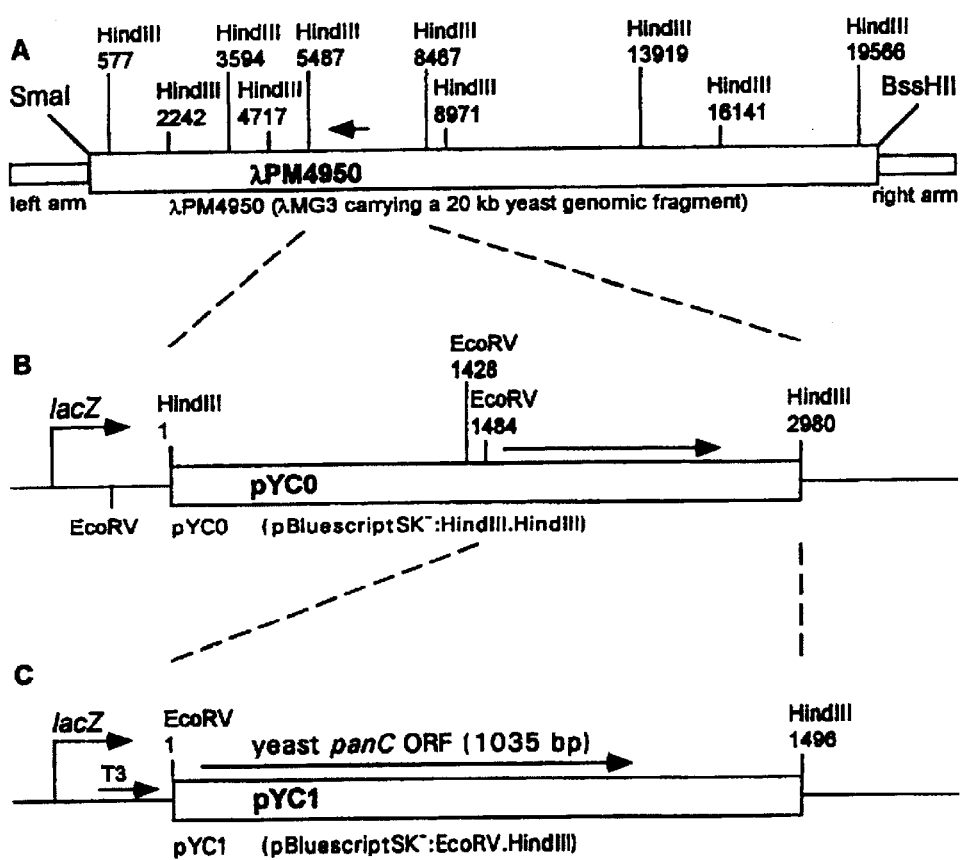
Referring to FIG. 7, the subcloning of yeast pantothenate synthetase for expression in E. coli is depicted.
Figures 8, 8A, 8B:
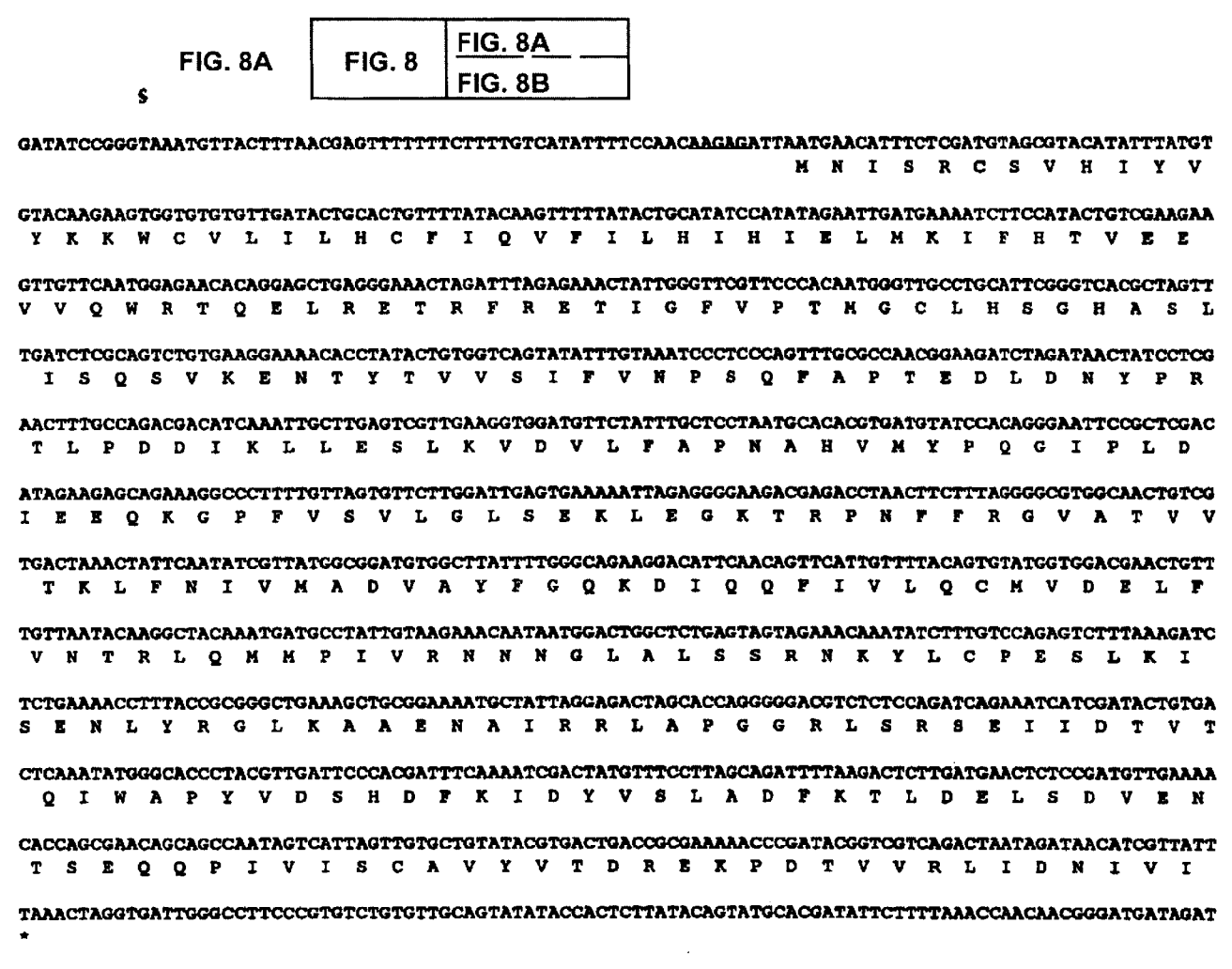

Comparison of the Amino Acid Sequences of Known, or Predicted to be, Pantothenate Sythetases When the amino acid sequences of known, or predicted to be, pantothenate sythetases were aligned (FIG. 6), the putative PS protein sequences of *S. cerevisiae* and *Schizosaccharomyces pombe* showed significant homology with *E. coli* PS. To confirm that the putative PS gene of *S. cerevisiae* did code for an enzyme with PS activity, a phage clone (PM4950) containing a 20 kb genomic fragment of the yeast chromosome IX which spans the putative PS gene was obtained from Dr. Carol Churcher, Sanger Centre, Hinxton Hall, Cambridge, UK The open reading frame coding for the putative gene was subcloned in two steps for expression in *E. coli* as shown in FIG. 7. In the resulting plasmid, pYC1, the yeast PS gene was under transcriptional control of the lacZ promoter. However, PS was not in frame with lacZ and therefore was not expressed as a fusion protein. The nucleotide sequence and putative translation product of the 1.5 kb EcoRV-HindIII genomic fragment in pYC1 are given in FIG. 8. Yeast PS functionally complemented the panC lesion in *E. coli* AT1371, confirming that the gene did code for a functional PS.

Example 4

Isolation of the 5' and the 3' Ends of Pantothenate Synthetase from *L. japonicus*

We expected plant PS to be located in the chloroplast, but there was no evidence from the PS cDNA clones of *L. japonicus* and *O. sativa* of any chloroplast transit signals. Furthermore, both enzymes were predicted to be cytosolic proteins by PSORT (Molecular Biology Tools, ExPasy WWW Server).

To clone 5' and 3' sequences of the PS gene inverse PCR (iPCR) was used. Genomic DNA was isolated from *L. japonicus* leaf tissue and prepared as described by Dellaporta et al (1983). Aliquots of Lotus genomic DNA (8 μg) were digested overnight with the following restriction endonucleases: BamHI, EcoRI, HindIII, NotI, SalI, XbaI, XhoI. DNA fragments were precipitated with isopropanol and resuspended in TE buffer before loading onto an agarose gel. After electrophoresis, gel pieces corresponding to fragment sizes of between 2 kb and 15 kb were isolated from the agarose gel, and purified using the US BioClean MP kit (United States Biochemical, Cleveland, Ohio, USA). Each reaction was ligated overnight at 14° C. with 1.5 units of T4 DNA ligase in conditions which promote intra-molecular ligation. DNA was precipitated from the ligation mix with isopropanol, washed with ethanol, resuspended in sterile distilled water and used as templates in the following PCR step.

PCR amplification was carried out using the Expand High Fidelity PCR system from Boehringer Mannheim, FRG, adopting the manufacturers protocol for amplification of DNA of a size of up to 3 kb. The design of *L. japonicus* PS-specific primers Li5 and Li3 (Li5: dCG GGATCCATGGTGGGAACGAGGGCGATGAG (SEQ ID NO:15) and Li3: dCATC AAGCTTATGTATCAAAGTGCCCCAGG (SEQ ID NO:16)) folowed the general protocols for iPCR by Ochman et al. (1989). Restriction sites incorporated into the Li primers are HindIII in Li3 and BamHI in Li5 (underlined). Of all seven templates only the BamHI-derived circular Lotus library was effective in iPCR reactions. A single product of 750 bp was obtained with a minor contaminant at about 250 bp. This iPCR product was cleaved by BamHI as expected and was cloned into the pCRII vector using the PCR T/A cloning kit (Invitrogen, NV Leek, Netherlands following the manufacturer's instructions). The EcoRI insert of the resulting plasmid was sequenced at the Centre of Molecular Recognition, Department of Biochemistry, University of Cambridge (FIG. 9A). By comparison with the *L. japonicus* PS sequence, the genomic iPCR product matched the cDNA's 3' and 5' ends and was assumed to contain authentic PS flanking regions. The annotated nucleotide sequence is shown in FIG. 9B.

While primer and cDNA sequences were straightforwardly identified within the iPCR product, analysis of the flanking regions was more difficult, since intron-exon borders can only be identified with some confidence. Prediction of splice sites according to Hebsgaard et al. (1996) at the NetPlantGene Server (Center for Biological Sequence Analysis, Technical University of Denmark, Lyngby, Denmark), suggested possible donor splice sites at positions 258 and 281, and possible acceptor splice sites at positions 179, 316, 338 and 536 in the sequence given in FIG. 9B. These sites were found in the low probability threshold mode of the program to include nearly all true sites. Intriguingly, none of these splice sites are situated within regions corresponding to cDNA.

There is one sequence feature of value regarding the question of the true translation start site within PS. This is a stop codon in the 5' flanking region, 21 bases upstream from the putative initiation site, which is in frame with the PS ORF. If this stop codon forms part of the PS 5'-leader sequence as was implied in the splice site predictions, the ORF as encoded by the PS cDNA could safely be assumed to be complete. Specifically, this conclusion is conditional upon the absence of acceptor splice sites in between stop codon and cDNA start. The primary sequence information as such seems reliable firstly because a DNA-polymerase with proof reading activity was used in the PCR amplification and secondly because the chromatograms generated in two sequencing runs are both unambiguous.

Example 5

Cloning Pantothenate Synthetase from *Lotus japonicus* into an Expression Vector An expression cassette was generated from the *L. japonicus* cDNA for PS using the PCR method of MacFerrin et al (1990). Lotus panC ORF was amplified from ca. 25 ng of plasmid pLC, using the primers LC5 and LC3. LC5 was designed to the start, ATG, codon of PS with an XbaI site highlighted in bold type and a ribsome binding site, underlined, included in the PCR primer: dCGCGCTCTAGA AGGAGGAATTTAAAATGGCACCAATGGTGATATC TGAT (SEQ ID NO:17). LC3 was designed to include the stop codon (TTA) of the ORF and an XhoI restriction site, in bold, in the PCR primer: dGCGCGCTCGAGTTA-CAAGTTGATTTCTATGTT (SEQ ID NO:18).

The PCR product was cloned into pBLUESCRIPT SK⁻ (Stratagene Ltd. Cambridge Innovation Centre, 140 Cambridge Science Park, Milton Road, Cambridge, CB4 4GF, UK) using the XbaI and XhoI restriction sites incorporated in the primers, and the resulting clone was referred to as pSKL. The expression cassette was designed to contain the *L. japonicus* PS ORF as demonstrated FIG. 10. The correct construct was confirmed by DNA sequence analysis (data not shown).

Example 6

Expression of Pantothenate Synthetases from *Lotus japonicus*, *Oryza sativa*, and *Saccharomyces cerevisiae* in *Escherichia coli*

*L. japonicus* PS was expressed in an *E. coli* panC mutant AT1371 because wild-type *E. coli* strains have considerable PS activity which would make purification of the recombinant enzyme more difficult. *E. coli* AT1371 (panC) transformed with the Lotus panC overexpressing plasmid pSKL was grown from single colonies overnight in 10 ml LB cultures containing 100 $\mu$g/ml ampicillin. Four 500 ml aliquots of 2YT medium (1.6% (w/v) bactopeptone, 1.0% (w/v) yeast extract and 0.5% (w/v) NaCl in water) in 2 liter flasks containing 60 $\mu$g/ml ampicillin and 20 $\mu$g/ml IPTG were each inoculated with 5 ml of overnight culture and incubated at 37° C. with shaking (190 RPM) for 10 hours before harvesting. *E. coli* cells were recovered by centrifugation (10 min, 5000 RPM) and immediately resuspended in 20 ml of buffer A (50 mM Tris.HCl, 1 mM EDTA, 0.1 mM DTT, pH 8.0). Cells were lysed by sonication. Two equal aliquots of the cell suspension were each sonicated 6 times for 30 seconds on ice, with a 30 second pause between each burst. Cell debris was removed by centrifugation (30 min, 12000 RPM) and the crude extract was assayed for enzymatic activity.

Along with the Lotus PS expression clone pSKL, expression of PS activity was examined with all other available PS clones, that is the lacZ-PS fusion clones of Lotus and rice (pLC and pRC, respectively), yeast panC (pYC1) and *E. coli* panC (pCL). However, unlike pSKL clones, no attempt was made to optimise expression. Crude extracts from *E. coli* AT1371 transformed with these pantothenate synthase clones or with vector alone were assayed for pantothenate synthase activity using either pantoate or pantoyl-lactone as substrate. Crude extract from wild type *E. coli* was also assayed, and the results are shown in the appended table (Table 1) which includes previously reported PS activities. In all cases examined enzyme activities were much higher with pantoate than with pantoyl-lactone. Given that purified *E. coli* PS had no activity toward pantoyl-lactone (Miyatake et al., 1979), the residual activities seen here with the latter substrate are likely due to a hydrolysing activity present in the cell extracts. An activity that catalyses hydrolysis of pantoyl-lactone was previously implied by Maas (1952a and 1952b). Failure to detect activity in samples derived from the Lotus or rice panC-lacZ fusion clones indicates lack of expression of enzymatically active PS. However, these clones were successfully used to complement a panC lesion in *E. coli* and therefore must express at least low levels of PS activity. Activities found in wild type *E. coli* or AT1371 transformed with vector alone are in accordance with previously reported values.

TABLE 1

Expression of pantothenate synthetases in *E. coli* AT1371 (panC) and wild type strains

| | | Specific Activity [U/mg] | | |
|---|---|---|---|---|
| *E. coli* strain | Vector | Pantoate or | Pantoyl-lactone | Reference |
| AT1371 (panC) | PskL Lotus PS | 8.7 | not detected | this study |
| AT1371 (panC) | PLC Lotus PS-lacZ | not detected | not detected | |
| AT1371 (panC) | PRC rice PS-lacZ | not detected | not detected | |
| AT1371 (panC) | PYC1yeast PS | 88.0 | 3.1 | |
| AT1371 (panC) | PCL *E. coli* PS | 957.4 | 6.0 | |
| AT1371 (panC) | PBluescript | not detected | not detected | |
| K12 (wild type) | | 13.4 | | |
| K12 (wild type) | | 8.1–8.7 | <0.001 (not detected) | Cronan et al. (1982) |
| AT1371 (panC) | | | | |
| B (wild type) | | 4.1 | | Miyatake et al. (1979) |
| W (wild type) | | 1.3 | | Pfleiderer et al. (1961) |

Example 7

Purification of Recombinant *Lotus japonicus* Pantothenate Synthetase Expressed in *Escherichia coli*

A crude extract of *E. coli* AT1371 transformed with the Lotus panC expression clone pSKL was prepared as described in Example 6. Starting from this crude extract, PS was essentially purified in two steps, ammonium sulphate fractionation and anion exchange chromatography. To the cleared extract (28 ml), a saturated solution of $(NH_4)_2SO_4$ (12 ml) was added to reach a final concentration of 30% $(NH_4)_2SO_4$. The solution was kept on ice for 1 hour with stirring to allow protein aggregates to form. Insoluble protein was removed by centrifugation (12,000 RPM, 30 minutes) at 4° C. The supernatant was recovered (36 ml) and brought to 40% $(NH_4)_2SO_4$ saturation by addition of 6 ml of saturated $(NH_4)_2SO_4$ solution. The solution was incubated and centrifuged as before. Pelleted protein aggregates were dissolved in 5 ml of buffer A and dialysed against 2 litres of buffer A overnight at 4° C. The dialysed solution was centrifuged at 12,000 RPM for 30 minutes, and the supernatant was directly used in the anion exchange chromatography step.

The sample (5 ml) was loaded onto a Pharmacia FPLC MonoQ HR10/10 column previously equilibrated in buffer A. The column was washed with equilibration buffer until $A_{280}$ of the eluate was constant and below 0.1, and a constant flow rate of 2 ml/min was maintained throughout the run. Protein was eluted in a linear gradient (80 ml) of 0–250 mM KCl in buffer A, and 1 ml fractions were collected throughout the gradient and assayed for PS activity. FIG. 6 shows the PS activity (FIG. 11A) and protein (FIG. 11B) profiles of this chromatographic step. The majority of PS activity eluted at ca. 100 mM KCl concentration. A second peak of PS activity eluted well separated from the first at just under 200 mM KCl along the gradient. This peak was broader than the first one and contained a much smaller but significant amount of activity. Since a homogenous overexpression product would principally be expected to elute in a single peak, separation of PS activity into two peaks was at first held to be an artifact. However, using a different column (MonoQ HR16/10) or changing gradient parameters including a solute change from KCl to ammonium acetate made no difference to the elution pattern. Physical differences in between the PS proteins in peaks one and two that could account for this behaviour may be due to differential folding or post-translational processing. The fractions with highest PS activities in either peak were pooled as indicated in FIG. 11A. Fractions 29 through 32 within the first peak gave sample PS-I (4 ml) which recovered 73% of PS activity loaded onto the column. Likewise, fractions 57 through 60 from the second peak were pooled to give PS-II (4 ml) containing 12% of the original PS activity. Samples PS-I and PS-II together contained 21.7 mg of PS.

Both, PS-I and PS-II were dialysed against 1 litre of buffer A overnight at 4° C. and centrifuged to precipitate insoluble protein. 500 µl aliquots of both PS-I and PS-II were loaded onto a Pharmacia Superose 6 column equilibrated in buffer A, maintaining a constant flow rate of 0.5 ml per minute and collecting 1 ml fractions. PS activity from both samples eluted in single peaks at an equal retention volume after injection, indicating a similar native molecular weight for PS-I and PS-II. This step offers no further purification of PS. In fact, specific activity was slightly decreased in both cases as can be seen from the purification summary in Table 2. However, SDS-PAGE (Laemmli, 1970; Sambrook et al., 1989) analysis of these samples revealed removal of some protein contaminants through gel filtration. Fractions 16 and 17 were pooled in each case to give samples PS-I/GF and PS-II/GF. Physical characterisation of recombinant PS is dealt with in the next section and was carried out on both PS-I and PS-II while kinetic analysis (Example 9) was restricted to PS-I.

TABLE 2

Summary of the purification procedure for recombinant
*L. japonicus* pantothenate synthetase. PS was assayed using
pantoate and β-alanine at final concentrations of 1 mM and 10 mM,
respectively. Protein was assayed according to the method of
Bradford (1976), using the Bio-Rad Protein reagent and microprotein
assay in accordance with the manufacturer's instructions.
Bovine serum albumin was used to calibrate the assay.

| Sample | total protein (mg) | total Units (nmoles/min) | Specific. Activity (U/mg) | re-covery (%) | purification |
|---|---|---|---|---|---|
| Cleared extract | 908.6 | 27410.2 | 30.2 | (100) | (1) |
| $(NH_4)_2SO_4$ 30–40% | 209.7 | 33030.6 | 157.5 | 121 | 5.2 |
| MonoQ - PS-I | 17.8 | 24160.8 | 1357.3 | 88 | 44.9 |
| MonoQ - PS-II | 3.9 | 4070.7 | 1038.5 | 15 | 34.1 |
| Superose 6 - PS-I[a] | 2.16 | 2386.6 | 1104.9 | 79[b] | 36.3 |
| Superose 6 - PS-II[a] | 0.44 | 400.8 | 911.0 | 79[b] | 29.9 |

[a]Aliquots of the MonoQ - PS-I - pool (2.2 mg of protein in 0.5 ml) or the MonoQ -PS-II - pool (0.5 mgs of protein in 0.5 ml) were purified further by Superose 6 gel filtration. PS activity from both PS-I and PS-II eluted in a single peak at identical retention volumes.
[b]The recovery is expressed with respect to the activity loaded onto the gel filtration column--;

Example 8

Characterisation of the Recombinant *Lotus japonicus* Pantothenate Synthetase In order to confirm the identity of the overexpressed Lotus PS, N-terminal protein sequencing (Table 3) and amino acid analysis (Table 4) was carried out at the Protein and Nucleic acid Chemistry Facility in the Department of Biochemistry, University of Cambridge on an applied Biosystems 477A Protein Sequencer for both PS-I and PS-II.

TABLE 3

N-terminal protein sequences of PS-I and PS-II proteins and predicted sequence for *L. japonicus* pantothenate synthetase

| | | |
|---|---|---|
| Predicted sequence (a): | MAPMVISD K D E M R K W S R | (SEQ ID NO: 19) |
| 1° sequence (b): | P M V I S D K D E M R K W S R | (SEQ ID NO: 20) |
| 2° sequence (b): | A P M V I S D K D E M R K W S R | (SEQ ID NO: 21) |

(a) N-terminal protein sequence predicted from the *Lotus japonicus* ORF for PS (cf. FIG 1.2). The residues underlined correspond to the nucleotide sequence of the PCR primer used in the production of the over-expression clone.
(b) Identical N-terminal protein sequences were obtained for PS-I and PS-II. The molar yield of secondary sequence as compared to primary sequence was ca. 70% in case of PS-I and ca. 30% for PS-II Alignment of N-terminal sequences obtained for PS-I and PS-II to the theoretical N-terminus of *L. japonicus* PS in Table 3 demonstrated that the purified recombinant protein is PS from *L. japonicus*. The overexpressed protein was apparently processed at the N-terminus, and the majority of both PS-I and PS-II lacked two N-terminal residues (methionine and alanine). However, some of the protein only lacked methionine giving rise to the secondary sequences observed. PS-I and PS-II differ somewhat with respect to the proportions of these differentially processed species. This can be seen from the relative yields at which primary and secondary sequences were obtained. The less abundant protein species with N-terminal alanine sequenced at an average yield comprising 70% (PS-I) or 40% (PS-II) of that seen for the primary sequence.

The theoretical molecular weight of recombinant *L. japonicus* PS is 34.2 kD, and this value is in reasonable agreement with the subunit weight obtained by SDS-PAGE analysis of the purified overexpression product (ca. 37 kD). The native molecular weight of PS-I or PS-II was estimated by gel filtration to be 72.8 kD implying the native protein is a homodimer.

More accurate determination of the Lotus PS subunit molecular weight was achieved by electrospray mass spectroscopy ESMS (carried out on an electrospray ionisation (positive ion mode) quadrapole mass spectrometer (BioQ; VG, Manchester, UK) using software supplied by the manufacturer). The transformed mass data revealed the presence of two protein species both in PS-I and PS-II which differ by 72.3 Da and 70.3 Da, respectively. This corresponds well to the theoretically expected mass difference in between presence or absence of an N-terminal alanine, that is 71.0 Da. Protein sequencing of recombinant PS had already shown that the N-terminal methionine was missing from the overexpression product while the following alanine residue was only partially removed. The main ESMS signal (100%) belongs to the lighter species and does therefore in all likelihood correspond to PS with N-terminal proline. Likewise, the secondary signals obtained at 75% (PS-I) or 40% (PS-II) relative intensity are due to PS with N-terminal alanine. As was concluded from the N-terminal sequencing data, the relative proportions of lighter and heavier PS species obtained here indicate PS-II was more efficiently processed than PS-I.

TABLE 4

Amino acid compositions obtained by amino acid analysis for PS-I and PS-II.

| Amino acid | expected value | integer fit of measured mole ratios to expected values | |
|---|---|---|---|
| | | PS-I | PS-II |
| Cys | 5 | 5.64 | not determined |
| Asp | 33 | 35.24 | 33.67 |
| Thr | 6 | 6.14 | 6.71 |
| Ser | 23 | 18.79 | 19.96 |
| Glu | 30 | 24.78 | 25.19 |
| Gly | 26 | 28.50 | 26.20 |
| Ala | 19 | 20.02 | 19.76 |
| Val | 33 | 30.70 | 32.76 |
| Met | 7 | 7.03 | not determined |
| Ile | 20 | 20.37 | 19.84 |
| Leu | 22 | 24.56 | 23.78 |
| Tyr | 7 | 7.01 | 6.5 |
| Phe | 13 | 15.07 | 13.01 |
| His | 8 | 7.64 | 12.11 |
| Lys | 20 | 20.89 | 22.52 |
| Arg | 17 | 16.97 | 16.17 |
| Pro | 12 | 11.67 | 10.82 |
| Trp | 5 | not determined | not determined |
| 306 residues | | | |

The *L. japonicus* PS ORF encodes a polypeptide of 308 residues with a predicted molecular weight of 34.2 kDa, and the processed recombinant protein (3-proline through 308-leucine) has a theoretical mass of 34,037.7 Da.

This is only in rough accordance with the weights obtained for PS-I (33,969.0±12.3 Da) and PS-II (33,967.0±10.2 Da), that is these proteins are lighter than expected by 68.7 Da and 70.7 Da, respectively. Given the accuracy of ESMS mass determinations, this discrepancy is presumably not due to a machine artifact. A possible explanation for the mass differences would be a mutation in the overexpression clone that might have been introduced through the PCR amplification of the *L. japonicus* panC expression cassette. However, the PCR step in question was carried out using a polymerase mix including a proof-reading activity, and, as mentioned earlier, no nucleotide sequence changes were found in between panC cDNA and expression cassette. Alternatively, the overexpressed PS may have been further processed at the C-terminus, for example.

Example 9

A High-throughput Assay for Pantothenate Synthetase Activity

Three different assays have been reported previously for measuring PS activity (see above). The assays described by Maas (1950a and 1950b) and Miyatake et al (1979) are either microbiological or radiometric, while the number of auxilary enzymes and substrates required for the assay developed by Pfleiderer et al (1960) makes this assay cumbersome, expensive, and limited in its application to low throughput screening only. Hence, all three assays are unsuitable for the large scale high throughput biochemical screening of compounds necessary to discover new inhibitors of PS.

The applicants have developed in vitro assays which can be employed for high throughput biochemical screening for detecting inhibitors of this enzyme, to the use of these assays in the development of novel herbicides and in determining their mode of action, and to biological active inhibitors of pantothenate biosynthesis and herbicides obtained thereby. The assays are designed to measure the pyrophosphate liberated in the PS reaction either directly with a modified version of the calorimetric assay for the determination of inorganic pyrophosphate originally described by Chang et al. (1983); or after its conversion with inorganic pyrophosphatase to inorganic phosphate, which is then determined with modified versions of the calorimetric assays for the determination of inorganic phosphate originally described by Lanzetta et al. (1979) or Chifflet et al. (1988). The assays are carried out at room temperature, preferably on a microtiter scale.

1. The preferred assay mixture to colorimetrically measure the pyrophosphate liberated in the PS reaction comprises 100 $\mu$mol Tris.HCl (pH 8.0), 10 $\mu$mol MgSO$_4$, 5 $\mu$mol ATP, 10 $\mu$mol β-alanine, 0.5 $\mu$mol pantoate and pantothenate synthetase in a total volume of 100 $\mu$l. After a suitable incubation period the PS reaction is terminated by the addition of 10 $\mu$l of a 0.8 M 2-mercaptoethanol in a 10% (w/v) solution of sodium dodecylsulfate followed by the addition of 50 $\mu$l of a 2.5% (w/v) solution of ammoniumheptamolybdate in 5 N sulfuric acid. After 20 minutes incubation at room temperature the intensity of the colour complex is determined by measuring the extinction at 620 nm. The amount of pyrophosphate liberated in the PS reaction is determined by reference to a standard curve generated from suitable amounts of pyrophosphate by using the difference of extinction at 620 nm between a complete PS assay mixture and a PS assay mixture lacking pantoate. One unit of PS activity is defined as the amount of enzyme producing 1 nmole of pyrophosphate per minute, and specific activity is expressed as units per milligram of protein.

2. The preferred assay mixture to measure the pyrophosphate liberated in the PS reaction after its conversion with inorganic pyrophosphatase to inorganic phosphate comprises 100 $\mu$mol Tris.HCl (pH 8.0), 10 $\mu$mol MgSO$_4$, 5 $\mu$mol ATP, 10 $\mu$mol γ-alanine, 0.5 $\mu$mol pantoate, 1.0 unit yeast inorganic pyrophosphatase and pantothenate synthetase in a total volume of 100 $\mu$l. After a suitable incubation period the PS reaction is terminated either a) by the addition of 100 $\mu$l of a reagent mixture comprising 62.3 □g malachite green hydrochloride, 1.9 mg ammoniumheptamolybdate and 0.5% (v/v) of a suitable detergent (for example Triton X-100, Tween-80 or Tergitol NPX) in 1.88 N hydrochloric acid. The resulting colour complex is stabilised by the addition after 1 minute of 50 $\mu$l of a 26% (w/v) solution of trisodium citrate dihydrate in water and after an additional 45 minutes incubation at room temperature the intensity of the colour complex is determined by measuring the extinction at 620 nm. The amount of inorganic phosphate liberated in the PS reaction is determined by reference to a standard curve generated from suitable amounts of inorganic phosphate by using the difference of extinction at 620 nm between a complete PS assay mixture and a PS assay mixture lacking pantoate. Since there are 2 molecules of inorganic phosphate liberated for every molecule of pyrophosphate formed in the PS reaction, one unit of PS activity is defined as the amount of enzyme producing 2 nmoles of inorganic phosphate per minute, and specific activity is expressed as units per milligram of protein; or b) by the addition of 100 $\mu$l of a reagent mixture comprising 3 mg ascorbic acid, 0.5 mg ammoniumheptamolybdate and 1 mg sodium dodecylsulfate in 0.7 N hydrochloric acid. The resulting colour complex is stabilised by the addition after 7 minutes of 50 $\mu$l of a 6% (w/v) solution of trisodium citrate dihydrate in water and after an additional 20 minutes incubation at room temperature the intensity of the colour complex is determined by measuring the extinction at 620 nm. The amount of inorganic phosphate liberated in the PS reaction is determined by reference to a standard curve generated from suitable amounts of inorganic phosphate by using the difference of extinction at 620 nm between a complete PS assay mixture and a PS assay mixture lacking pantoate. Since there are 2 molecules of inorganic phosphate liberated for every molecule of pyrophosphate formed in the PS reaction, one unit of PS activity is defined as the amount of enzyme producing 2 nmoles of inorganic phosphate per minute, and specific activity is expressed as units per milligram of protein.

In order to determine the linear range of the assay used here, recombinant PS purified through the anion exchange chromatography step was assayed by method 2a, using final β-alanine and pantoate concentrations of 10 mM and 0.5 mM, respectively. When various amounts of PS were assayed, a proportional relationship of inorganic phosphate formed and enzyme amount was obtained in between 1 and 4 $\mu$g of protein (FIG. 12A). Furthermore, when a given amount of PS was assayed for different time periods, a proportional relationship of inorganic phosphate formed and incubation time is obtained in between 0 and 20 minutes of incubation (FIG. 12B).

Example 10

Biochemical Properties of Recombinant Lotus japonicus Pantothenate Synthetase The recombinant *L. japonicus* enzyme investigated here was found to require pantoate, β-alanine, ATP and $Mg^{2+}$ for activity. The pantoate analogues pantoyl-lactone and ketopantoate were not active as substrates in the place of pantoate. When present at 10-fold excess over pantoate, these analogues did not effect significant inhibition (Table 5).

TABLE 5

Substrate specificity of the recombinant *L. japonicus* pantothenate synthetase.

| Pantoate | β-alanine | change from standard assay | activity (units) | yield (%) |
|---|---|---|---|---|
| 0.1 mM | 1 mM | — | 12.51 | (100) |
| 0.1 mM | — | — | 0 | 0 |
| — | 1 mM | — | 0 | 0 |
| — | 1 mM | pantoyl-lactone (1.0 mM) | <0.1 | <1 |
| — | 1 mM | pantoyl-lactone (10 mM) | 0.15 | 1 |
| — | 1 mM | ketopantoate (1.0 mM) | 0 | 0 |
| — | 1 mM | ketopantoate (10 mM) | 0 | 0 |
| 0.1 mM | 1 mM | pantoyl-lactone (1.0 mM) | 11.53 | 92 |
| 0.1 mM | 1 mM | ketopantoate (1.0 mM) | 12.18 | 97 |

With 100 mM Tris.HCl buffer optimal PS activity was achieved at pH 8.0. Activity decreases sharply towards more acidic pH's and is nil at pH 7.0, while there is only a slight decrease towards higher pH's with ca. 75% activity left at pH 9.0.

$K_m$ and $V_{max}$ constants for pantoate and ⊖-alanine were determined by measuring the effect of substrate concentration on the reaction rate. Either pantoate or β-alanine were kept at a constant concentration of either 0.5 or 20 mM, and activity assays were carried out using variable concentrations of the other. Plotting the PS activity as a function of substrate concentration according to Lineweaver and Burk (1934) and Eadie (1942) and Hofstee (1959) revealed the kinetic constants as listed in Table 6.

TABLE 6

Steady state kinetic constants for the recombinant Lotus pantothenate synthetase.

| Substrate | $K_m^{(a)}$ [µM] | $V_{max}^{(a)}$ [units] | $k_{cat}^{(b)}$ [sec$^{-1}$] |
|---|---|---|---|
| Pantoate | 45 (LB) | 11.36 (LB) | 0.63 |
| (β-alanine at 20 mM const.) | 44 (EH) | 10.98 (EH) | |
| β-alanine | 990 (LB) | 9.52 (LB) | 0.54 |
| (pantoate at 0.5 mM const.) | 986 (EH) | 9.51 (EH) | |

[a] Kinetic constants were derived according to Lineweaver-Burk (LB) and Eadie-Hofstee (EH).
[b] Calculation of $k_{cat}$ is based on the $V_{max}$-mean from LB- and EH-determinations using the known enzyme amount per assay and a molecular weight of 34 kD.

Lotus PS suffers from substrate inhibition by pantoate, which becomes significant at pantoate concentrations of 400 µM or higher. The effect of pantoate concentration on $K_m$ and $V_{max}$ for β-alanine was as expected for pure uncompetitive inhibition, that is both constants decreased with increasing pantoate concentration while their ratio remained constant. $K_m$ over $V_{max}$ for β-alanine derived from Lineweaver-Burk analysis equalled 0.106 and 0.104 for pantoate concentrations of 20 mM and 0.5 mM, respectively. When the rate equation for uncompetitive substrate inhibition was fitted to the PS activity data for pantoate, values of 42±2 µM and 5.33±0.34 mM were derived for $K_S$ and $K'_S$, respectively. $V_{max}$ is 11.03±0.19 units in this fit which is equal to a $k_{cat}$ value of 0.625±0.011 sec$^{-1}$. The $K_S$ and $k_{cat}$ values are very similar to $K_m$ and $k_{cat}$ as derived from linearised plots of activity data.

Using the rate equation for uncompetitive substrate inhibition and the values for $K_S$ and $K'_S$ obtained in the fit, an optimal pantoate concentration of 470±30 µM was calculated.

PS was also assayed in the presence of various compounds that might be expected to possess regulatory properties towards the enzyme. Among these compounds are the intermediates of pantothenate biosynthesis as well as coenzyme A. As coenzyme A plays a prominent role in fatty acid synthesis and degradation, various acyl forms of coenzyme A and free fatty acids were also included. PS was not assayed at optimal substrate concentrations, but pantoate and β-alanine were present at concentrations close to the respective $K_m$ values (0.1 mM and 1 mM). Table 7 lists the compounds tried and their effect on PS activity which is expressed percentage of activity in an assay without additions.

TABLE 7

Activity of recombinant Lotus pantothenate synthetase in the presence of various potential effectors.
Pantothenate synthetase activity obtained with individual compounds is expressed as a percentage of activity in an assay without effector. The assay was carried out using pantoate and β-alanine at concentrations of 0.1 mM and 1.0 mM, respectively.

| Compound | Concentration [mM] | Final activity [%] |
|---|---|---|
| — | — | (100) |
| a-KIVA | 1 | 89 |
| Ketopantoate | 1 | 97 |
| Pantoyl-lactone | 1 | 92 |
| Pantothenate | 1 | 98 |
| Pyrophosphate | 1 | 78 |
| CoenzymeA | 1 | 109 |
| | 0.2 | 106 |
| | 0.1 | 100 |
| Acetyl-coA | 0.100 | 93 |
| Malonyl-coA | 0.100 | 92 |
| Palmitoleoyl-coA | 0.022 | 114 |
| Oleoyl-coA | 0.024 | 108 |
| Palmitic acid | 0.060 | 115 |
| | 0.015 | 135 |
| | 0.002 | 133 |
| Palmitoleic acid | 0.100 | 100 |
| | 0.020 | 116 |

REFERENCES

Bradford, M. M. (1976) *Anal. Biochem.* 72, 248–254.
Chang, G. G., Pan, F. Yeh, C., and Huang, T. M. (1983) *Anal. Biochem.* 130, 171.
Chifflet, S., Torriglia, A., Chiesa, R., and Tolosa, S. (1988) *Anal. Biochem.* 168, 1.
Cronan, J. E., Littel, K. J. and Jackowski, S. (1982) *J. Bacteriol.* 149, 916–922.
Cronan, J. E. (1980) *J. Bacteriol.* 141, 1291–1297.
Dellaporta, S. L., Wood, J., and Hicks, J. B. (1983) *Plant Mol. Biol. Rep.* 1, 19–21.
Eadie, G. S. (1942) *J. Biol. Chem.* 146, 85.
Hebsgaard, S. M., Korning, P. G., Tolstrup, N., Engelbrecht, J., Rouze, P., and Brunak, S. (1996) *Nucl. Acids Res.* 24, 3439–3452.

Hofstee, B. H. J. (1959) *Nature* 184, 1296.
Lanzetta, P. A., Alvarez, L. J., Reinach, P. S. and Candia, O. A. (1979) *Anal. Biochem.* 100, 95–97.
Laemmli, U. K. (1970) *Nature* 227, 680–685.
Lineweaver, H., and Burk, D. (1934) *J. Am. Chem. Soc.* 56, 658.
Maas, W. K. (1952a) *J. Biol Chem.* 198, 23–32.
Maas, W. K. (1952b) *J. Bact.* 63, 227–232.
MacFerrin, K. D., Terranova, M. P., Schreiber, S. L., and Verdine, G. L. (1990) *Proc. Natl. Acad. Sci. USA* 87,1937–1941.
Miyatake, K., Nakano, Y., and Kitaoka, S. (1979) *Methods Enzymol.* 62, 215–219.
Ochman, H, Ajioka, J. W., Garza, D., and Hartl, D. L. (1989) *Inverse PCR in PCR Technology*, pp.105–112, Erlich, H. A. ed., Stockton Press, New York.
Pfleiderer, G., Kreiling, A., and Wieland, T. (1960) Biochem. Z. 333, 302–307.
Sambrook, J., Fritsch, E. F., and Maniatis, T. (1989) *Molecular Cloning: A Laboratory Manual,* 2nd Ed., Cold Spring Harbor Laboratory Press, Cold Spring Harbor, N.Y.
Senecoff, J. F. and Meagher, R. B. (1993). *Plant Physiol.* 102: 387–399.

What is claimed is:

1. An isolated DNA molecule encoding a protein from *Lotus japonicus*, which protein has pantothenate synthetase activity and which protein is located in the cytosol of *Lotus japonicus*.

2. An isolated DNA molecule according to claim 1, wherein the DNA molecule encodes a protein comprising the amino acid sequence set forth in FIG. 2 (SEQ ID NO: 4).

3. An isolated DNA molecule according to claim 2, wherein the DNA molecule comprises the nucleotide sequence set forth in FIG. 2 (SEQ ID NO: 1).

4. A non-naturally occurring chimeric gene comprising a promoter operably linked to the DNA molecule as claimed in claim 1.

5. A non-naturally occurring chimeric gene according to claim 4 wherein the protein comprises an amino acid sequence set forth in FIG. 2 (SEQ ID NO: 4).

6. A recombinant vector comprising the chimeric gene of claim 5, wherein the vector is capable of being stably transformed into a host cell.

7. A host cell stably transformed with the vector of claim 6 wherein the host cell is capable of expressing the DNA molecule.

8. A host cell according to claim 7 selected from the group consisting of a bacterial cell, a yeast cell and an insect cell.

9. A method of producing a protein, having pantothenate synthetase activity and being located in the cytosol of *Lotus japonicus*, in a host cell comprising,
 a) inserting a DNA molecule according to claim 1 into an expression cassette designed for the host;
 b) inserting the resultant molecule, containing individual elements linked in proper reading frame, into a vector capable of being transformed into the host cell;
 c) growing the thus transformed host cell in a suitable culture medium; and
 d) isolating the protein product either from the transformed cell or the culture medium or both and purifying it.

* * * * *

UNITED STATES PATENT AND TRADEMARK OFFICE
CERTIFICATE OF CORRECTION

PATENT NO.   : 6,630,331 B1
DATED        : October 7, 2003
INVENTOR(S)  : Abell et al.

It is certified that error appears in the above-identified patent and that said Letters Patent is hereby corrected as shown below:

<u>Column 3,</u>
Line 9, change "□-alanine" to -- β-alanine --

Figure 11:
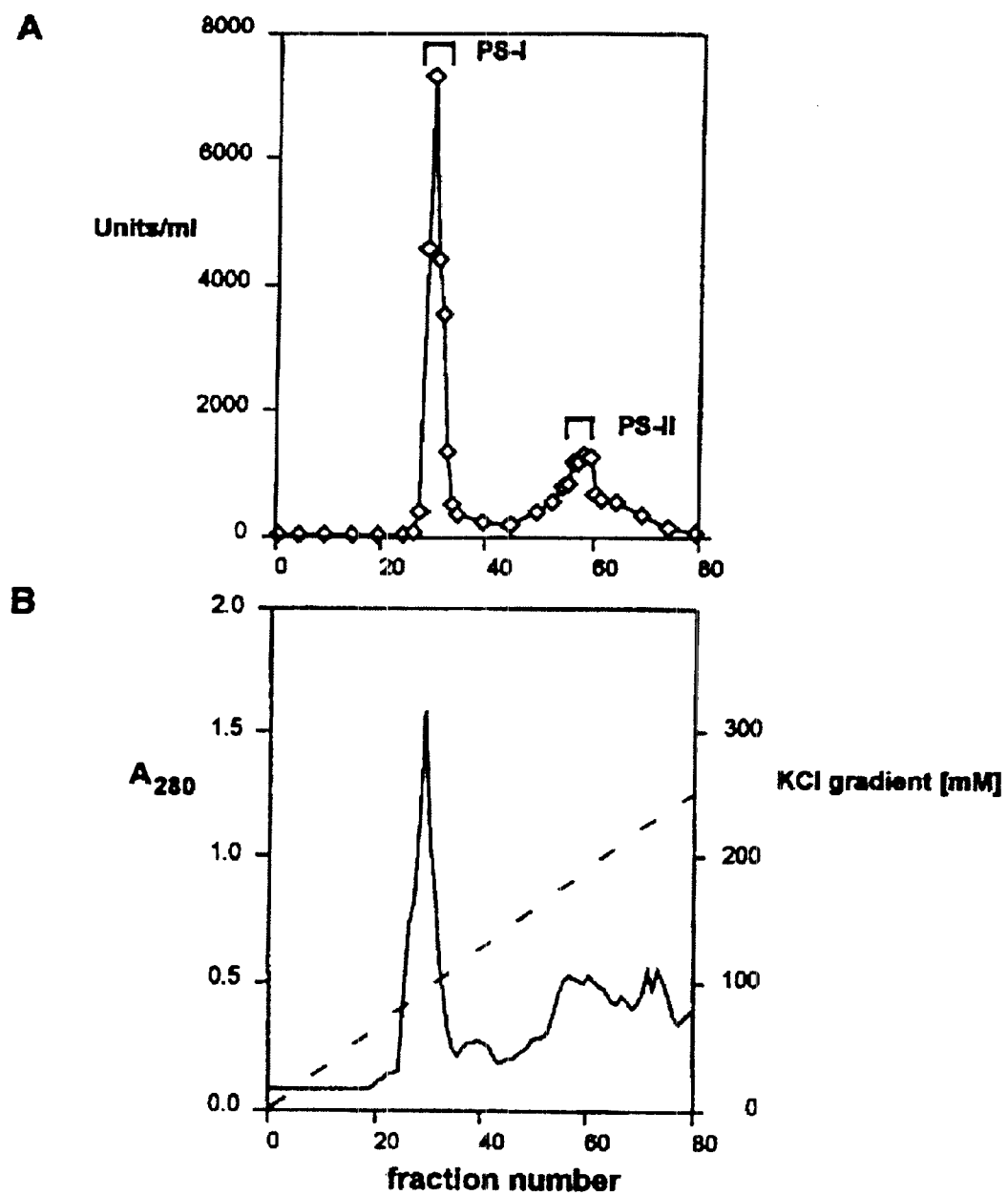
Referring to FIG. 11, there is shown the anion exchange chromatographs of recombinant *L. japonicus* pantothenate synthetase is shown. A sample of ammonium sulphate precipitated and dialyzed PS was subjected to anion exchange chromatography on a MonoQ HR10/10 column as described in Example 7.

<u>Column 11,</u>
Line 64, change "FIG. 6" to -- FIG. 11 --

<u>Column 16,</u>
Line 6, change "□g" to -- $\mu$g --

<u>Column 17,</u>
Line 34, change "θ-alanine" to -- β-alanine --

Signed and Sealed this

Seventeenth Day of February, 2004

JON W. DUDAS
*Acting Director of the United States Patent and Trademark Office*